United States Patent
Maruyama et al.

(10) Patent No.: US 9,150,537 B2
(45) Date of Patent: Oct. 6, 2015

(54) BICYCLIC COMPOUND AND USE THEREOF FOR MEDICAL PURPOSES

(75) Inventors: Toru Maruyama, Osaka (JP); Tohru Kambe, Osaka (JP); Shinsaku Yamane, Osaka (JP); Satoshi Nakayama, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 75 days.

(21) Appl. No.: 13/982,052

(22) PCT Filed: Jan. 26, 2012

(86) PCT No.: PCT/JP2012/051718
§ 371 (c)(1),
(2), (4) Date: Jul. 26, 2013

(87) PCT Pub. No.: WO2012/102355
PCT Pub. Date: Aug. 2, 2012

(65) Prior Publication Data
US 2013/0310438 A1 Nov. 21, 2013

(30) Foreign Application Priority Data

Jan. 27, 2011 (JP) ................................. 2011-014776

(51) Int. Cl.
*C07D 335/04* (2006.01)
*C07F 7/18* (2006.01)

(52) U.S. Cl.
CPC ............ *C07D 335/04* (2013.01); *C07F 7/1852* (2013.01)

(58) Field of Classification Search
CPC ..... C07D 335/04; C07F 7/1852; A61K 31/38
See application file for complete search history.

(56) References Cited

U.S. PATENT DOCUMENTS 4,230,721 A 10/1980 Gandolfi et al.
4,367,237 A * 1/1983 Wakatsuka et al. ........... 514/443

(Continued)

FOREIGN PATENT DOCUMENTS

JP 50-037780 A 4/1975
JP 53-084959 A 7/1978

(Continued)

OTHER PUBLICATIONS

Eyecare Specialties of Charleston (http://www.eyecarecharleston.com/eye-health/eye-diseases.html, acessed Dec. 4, 2014).*

(Continued)

*Primary Examiner* — Savitha Rao
*Assistant Examiner* — Angela Brown-Pettigrew
(74) *Attorney, Agent, or Firm* — Sughrue Mion, PLLC

(57) ABSTRACT

Provided is a compound which has strong intraocular pressure lowering action and has no side effect on eyes such as ocular stimulating property, humor protein rise etc.
Since a compound represented by the formula (I):

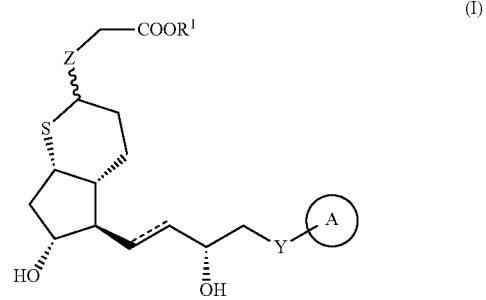

(I)

(wherein definition of each group is as described in the specification), or a salt thereof, a solvate thereof, or a prodrug thereof has strong intraocular pressure lowering activity and, further, has no side effect on eyes such as ocular stimulating property (hyperemia, corneal clouding etc.), aqueous humor protein rise etc., it has high safety, and can be an excellent agent for preventing and/or treating glaucoma etc.

9 Claims, 1 Drawing Sheet

(56) References Cited

U.S. PATENT DOCUMENTS

| | | | |
|---|---|---|---|
| 4,490,537 | A | 12/1984 | Johnson |
| 4,490,548 | A | 12/1984 | Johnson |
| 6,583,174 | B1 | 6/2003 | Ueno et al. |
| 2006/0035949 | A1 | 2/2006 | Donde et al. |

FOREIGN PATENT DOCUMENTS

| | | | |
|---|---|---|---|
| JP | 53-132573 | A | 11/1978 |
| JP | 55-073678 | A | 6/1980 |
| JP | 64-068367 | A | 3/1989 |
| WO | 01/27099 | A2 | 4/2001 |
| WO | 2007149829 | A2 | 12/2007 |
| WO | 2011/013651 | A1 | 2/2011 |

OTHER PUBLICATIONS

Wolff, Burger's medicinal Chemistry and Drug Discovery, vol. 1, Principles and Practice, John Wiley & sons, New York, 1997.*
West, Solid State Chemistry and Its Applications, John Wiley & Sons, 1984.*
European Search Report issued Dec. 3, 2012, in EP Application No. 10804397.7.
ISR (PCT/ISA/210) issued Sep. 14, 2010; in International Application No. PCT/JP2010/062587.
ISR (PCT/ISA/210) issued Mar. 13, 2012 in International Application No. PCT/JP2012/051718.
ISR (PCT/ISA/210) issued Mar. 13, 2012 in International Application No. PCT/JP2012/051721.
Search Report dated Jul. 17, 2014 issued by the European Patent Office in corresponding European Application No. 12739588.7.

* cited by examiner

BICYCLIC COMPOUND AND USE THEREOF FOR MEDICAL PURPOSES

TECHNICAL FIELD

The present invention relates to a compound represented by the formula (I):

[Chemical formula 1]

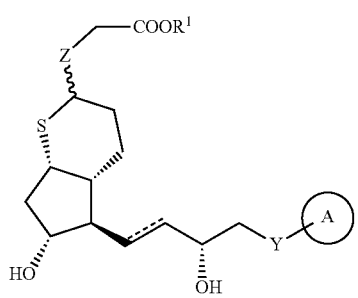

(I)

(wherein all symbols represent the same meanings as those described below), a salt thereof, or a solvate thereof, or a prodrug thereof (hereinafter, abbreviated as present invention compound in some cases).

BACKGROUND ART

Glaucoma is an ocular disease having the characteristic of a visual functional disorder which causes a transient or permanent visual field defect and decreased vision. This is derived from that since an aqueous humor is accumulated by a circulatory disorder of an aqueous humor, and an intraocular pressure is continuously increased, an optic nerve is compressed. Decrease in an intraocular pressure is effective for treatment of glaucoma and, in order to decrease an intraocular pressure, for example, drug treatment (eye drops, internal remedy, infusion treatment), laser treatment, or operation treatment is performed.

Previously, among prostaglandins (PGs) which are physiologically active substances, as those that decrease an intraocular pressure, PGFs and PGIs are known. Development of a drug for treating glaucoma or ocular hypertension is being progressed using derivatives of them, and there are some drugs which are actually sold (e.g. latanoprost etc.). However, the existing glaucoma treating drug alone is insufficient in intraocular pressure lowering action and, in at site of glaucoma treatment, since administration at a high concentration, or therapy of joint use of drugs having different mechanisms of action are being performed seeking stronger intraocular pressure lowering action, manifestation of side effects is feared. For this reason, drugs having stronger intraocular pressure lowering action, and high safety are desired.

Meanwhile, as the prior art of the present invention compound, the following PG derivatives are exemplified.

As a PG derivative having a bicyclic skeleton, for example, a compound represented by the formula (a):

[Chemical formula 2]

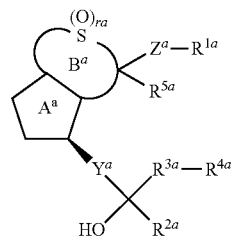

(a)

(wherein a ring $A^a$ represents

[Chemical formula 3]

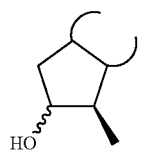

(wherein

[Chemical formula 4]

∼∼∼ represents α-configuration, β-configuration or a mixture thereof) etc., a ring $B^a$ represents

[Chemical formula 5]

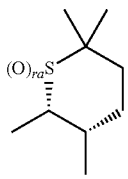

(wherein, ra represents 0, 1 or 2) etc., $Y^a$ represents an ethylene group, a vinylene group or an ethynylene group, $Z^a$ represents —$(CH_2)_{ma}$— (wherein ma represents 3, 4 or 5) etc., $R^{1a}$ represents —$COOR^{8a}$ (wherein $R^{8a}$ represents a hydrogen atom or an alkyl group of a C1-12 alkyl group etc.) etc., $R^{2a}$ represents a hydrogen atom etc., $R^{3a}$ represents a single bond or a C1-5 alkylene group etc., $R^{4a}$ represents a C1-8 alkoxy group, a halogen atom, a trifluoromethyl group, a phenoxy group optionally substituted with a C1-8 alkyl group, etc., and $R^{5a}$ represents a hydrogen atom etc.) is disclosed as a $PGI_1$ analogue, and described to be useful for contraception or menstruation control (see Patent Literature 1).

In addition, a compound represented by the formula (b):

[Chemical formula 6]

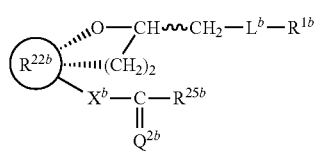

(wherein $L^b$ represents $-(CH_2)_{db}-$ (wherein db represents 1 to 5) etc., $Q^{2b}$ represents 0 etc., $R^{1b}$ represents $-COOR^{19b}$ (wherein $R^{19b}$ represents a C1-12 alkyl group or a hydrogen atom etc.) etc., a ring $R^{22b}$ represents

[Chemical formula 7]

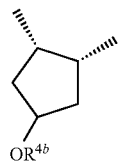

(wherein $R^{4b}$ represents a hydrogen atom etc.) etc., $R^{25b}$ represents

[Chemical formula 8]

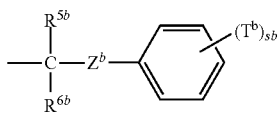

(wherein $R^{5b}$ and $R^{6b}$ represent a hydrogen atom etc., $Z^b$ represents $-O-$ etc., $T^b$ represents a C1-4 alkyl group, fluorine, chlorine, trifluoromethyl or $-OR^{7b}-$ (wherein $R^{7b}$ represents a C1-4 alkyl), sb represents 0, 1, 2 or 3, and $X^b$ represents

[Chemical formula 9]

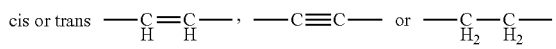

(a part of definitions of groups was extracted)) (see Patent Literature 2) is known.

Further, a compound represented by the formula (c):

[Chemical formula 10]

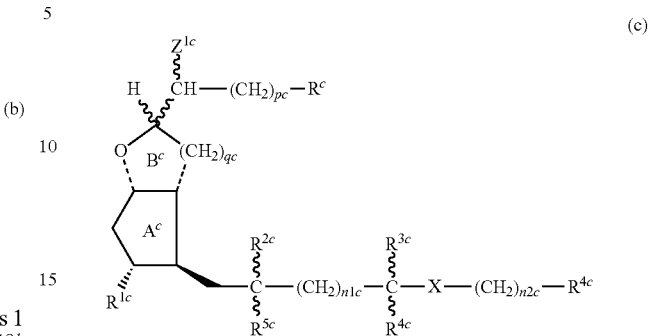

(wherein $R^c$ is selected from (a) a free carboxy group and an esterified carboxy group, etc., $Z^{1c}$ is hydrogen or a halogen, pc is 0 or an integer of 1 to 7, qc is 1 or 2, $R^{1c}$ is hydrogen, hydroxy, etc., $Y^c$ is selected from $-CH_2-CH_2-$,

[Chemical formula 11]

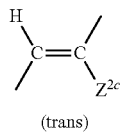

(trans)

(wherein $Z^{2c}$ is hydrogen or a halogen) etc., one of $R^{2c}$ and $R^{5c}$ is hydrogen, a C1-6 alkyl, etc., and the other is hydroxy, etc., $R^{3c}$ and $R^{4c}$ are the same or different and each are hydrogen, a C1-6 alkyl or fluorine, $n_{1c}$ and $n_{2c}$ are the same or different and each are 0 or an integer of 1 to 6, $X^c$ is selected from the group consisting of $-O-$, $-S-$ and $-(CH_2)_{mc}-$ (wherein mc is 0 or 1), and $R^{6c}$ is selected from the group consisting of hydrogen, a C1-4 alkyl, and an aryl unsubstituted or substituted with one or more substituents selected from the group consisting of a halogen and a C1-6 alkyl, etc.) is known (see Patent Literature 3).

Meanwhile, it has been reported that agonistic activity on an IP receptor among PG receptors causes hyperemia and rise in an aqueous humor protein, and inducement of stimulation on eyes has been feared (see Non-Patent Literatures 1 and 2). For this reason, since the compounds described in Patent Literatures 1, 2 and 3 which are PGI2 derivatives have agonistic activity on an IP receptor, there is a probability that property of stimulating eyes etc. are induced.

In addition, agonistic activity on EP2 and EP4 receptors is known to be involved in inflammatory response of eyes (see Non-Patent Literature 3).

The present invention compound is a compound which has low agonistic activity on an IP receptor and EP2 and EP4 receptors, and has selective agonistic activity on an FP receptor, but there is neither the description nor the suggestion regarding such a characteristic (selectivity) in any prior arts.

PRIOR ART LITERATURES

Patent Literatures

Patent Literature 1: U.S. Pat. No. 4,367,237
Patent Literature 2: U.S. Pat. No. 4,490,548
Patent Literature 3: JP-A No. 53-84959 gazette

Non-Patent Literatures

Non-Patent Literature 1: Investigative Ophthalmology & Visual Science, Vol. 28, p. 470-476, 1987
Non-Patent Literature 2: Investigative Ophthalmology & Visual Science, Vol. 23, p. 383-392, 1982
Non-Patent Literature 3: Ocular immunology and inflammation, Vol. 14, No. 3, p. 157-163, 2006

SUMMARY OF THE INVENTION

Problems to be Solved by the Invention

A compound which has strong intraocular pressure lowering action, and also has no fear of side effects on eyes is desired.

Means to Solve the Problems

In order to solve the aforementioned problems, the present inventors intensively studied to find out a compound which has improved selectivity on a PG receptor subtype, that is, a compound which has low agonistic activity on an IP receptor and EP2 and EP4 receptors, and has selective agonistic activity on an FP receptor and, as a result, completed the present invention.

That is, the present invention relates to:
[1] a compound represented by the formula (I):

[Chemical formula 12]

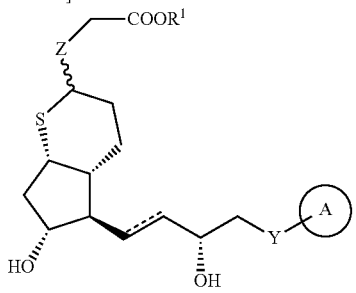

(wherein Z represents (1) —(CH$_2$)$_m$—, (2) —CH$_2$—O— or (3) —CH$_2$—S—; Y represents (1) —O—, (2) —S— or (3) —CH$_2$—; R$^1$ represents (1) a hydrogen atom or (2) a C1-6 alkyl group; a ring A represents a benzene ring optionally substituted with 1 to 5 substituents selected from the group consisting of (1) a halogen atom, (2) CF$_3$, (3) OCF$_3$, (4) a C1-4 alkoxy group, (5) a C1-4 alkyl group, (6) a hydroxyl group and (7) a nitrile group; m represents an integer of 1 or 2,

[Chemical formula 13]

----- represents a single bond or a double bond,

[Chemical formula 14]

represents α configuration,

[Chemical formula 15]

represents β configuration, and

[Chemical formula 16]

represents α configuration, β configuration or an arbitrary mixture thereof), or a salt thereof, a solvate thereof, or a prodrug thereof;
[2] the compound according to [1], wherein Z is —(CH$_2$)$_m$— (all symbols represent the same meanings as those described in [1]);
[3] the compound according to [1] or [2], wherein Y is —O—;
[4] the compound according to [1], wherein the compound represented by the formula (I) is a compound selected from the group consisting of
(1) methyl 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoate,
(2) methyl 4-{(2R,4aR,5R,6R,7aS)-6-hydroxy-5-[(1E,3R)-3-hydroxy-4-phenoxy-1-buten-1-yl]octahydrocyclopenta[b]thiopyran-2-yl}butanoate,
(3) 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoic acid,
(4) 4-{(2S,4aR,5R,6R,7aS)-6-hydroxy-5-[(1E,3S)-3-hydroxy-5-phenyl-1-penten-1-yl]octahydrocyclopenta[b]thiopyran-2-yl}butanoic acid,
(5) 4-{(2R,4aR,5R,6R,7aS)-6-hydroxy-5-[(1E,3R)-3-hydroxy-4-phenoxy-1-buten-1-yl]octahydrocyclopenta[b]thiopyran-2-yl}butanoic acid,
(6) 4-{(2S,4aR,5R,6R,7aS)-5-[(1E,3R)-4-(4-fluorophenoxy)-3-hydroxy-1-buten-1-yl]-6-hydroxyoctahydrocyclopenta[b]thiopyran-2-yl}butanoic acid,
(7) 4-{(2S,4aR,5R,6R,7aS)-5-[(1E,3R)-4-(3-chlorophenoxy)-3-hydroxy-1-buten-1-yl]-6-hydroxyoctahydrocyclopenta[b]thiopyran-2-yl}butanoic acid,
(8) 4-{(2S,4aR,5R,6R,7aS)-6-hydroxy-5-[(1E,3R)-3-hydroxy-4-(3-methylphenoxy)-1-buten-1-yl]octahydrocyclopenta[b]thiopyran-2-yl}butanoic acid,
(9) 4-{(2S,4aR,5R,6R,7aS)-5-[(1E,3R)-4-(2-fluorophenoxy)-3-hydroxy-1-buten-1-yl]-6-hydroxyoctahydrocyclopenta[b]thiopyran-2-yl}butanoic acid,
(10) 4-{(2S,4aR,5R,6R,7aS)-5-[(1E,3R)-4-(3-fluorophenoxy)-3-hydroxy-1-buten-1-yl]-6-hydroxyoctahydrocyclopenta[b]thiopyran-2-yl}butanoic acid,
(11) 4-[(2S,4aR,5R,6R,7aS)-6-hydroxy-5-{(1E,3R)-3-hydroxy-4-[3-(trifluoromethyl)phenoxy]-1-buten-1-yl}octahydrocyclopenta[b]thiopyran-2-yl]butanoic acid,
(12) 4-{(2S,4aR,5R,6R,7aS)-6-hydroxy-5-[(1E,3R)-3-hydroxy-4-(2-methoxyphenoxy)-1-buten-1-yl]octahydrocyclopenta[b]thiopyran-2-yl}butanoic acid,
(13) 4-{(2S,4aR,5R,6R,7aS)-6-hydroxy-5-[(1E,3R)-3-hydroxy-4-(3-methoxyphenoxy)-1-buten-1-yl]octahydrocyclopenta[b]thiopyran-2-yl}butanoic acid,
(14) 4-{(2S,4aR,5R,6R,7aS)-6-hydroxy-5-[(1E,3R)-3-hydroxy-4-(4-methoxyphenoxy)-1-buten-1-yl]octahydrocyclopenta[b]thiopyran-2-yl}butanoic acid,

(15) 4-{(2S,4aR,5R,6R,7aS)-6-hydroxy-5-[(1E,3R)-3-hydroxy-4-(2-methylphenoxy)-1-buten-1-yl]octahydrocyclopenta[b]thiopyran-2-yl}butanoic acid,
(16) 4-{(2S,4aR,5R,6R,7aS)-6-hydroxy-5-[(1E,3R)-3-hydroxy-4-(4-methylphenoxy)-1-buten-1-yl]octahydrocyclopenta[b]thiopyran-2-yl}butanoic acid,
(17) 4-{(2S,4aR,5R,6R,7aS)-5-[(1E,3R)-4-(4-chlorophenoxy)-3-hydroxy-1-buten-1-yl]-6-hydroxyoctahydrocyclopenta[b]thiopyran-2-yl}butanoic acid,
(18) 4-{(2S,4aR,5R,6R,7aS)-5-[(1E,3R)-4-(2-chlorophenoxy)-3-hydroxy-1-buten-1-yl]-6-hydroxyoctahydrocyclopenta[b]thiopyran-2-yl}butanoic acid,
(19) 4-[(2S,4aR,5R,6R,7aS)-6-hydroxy-5-{(1E,3R)-3-hydroxy-4-[2-(trifluoromethyl)phenoxy]-1-buten-1-yl}]octahydrocyclopenta[b]thiopyran-2-yl butanoic acid,
(20) 4-[(2S,4aR,5R,6R,7aS)-6-hydroxy-5-{(1E,3R)-3-hydroxy-4-[4-(trifluoromethyl)phenoxy]-1-buten-1-yl]octahydrocyclopenta[b]thiopyran-2-yl}butanoic acid,
(21) 4-{(2S,4aR,5R,6R,7aS)-6-hydroxy-5-[(3R)-3-hydroxy-4-phenoxybutyl]octahydrocyclopenta[b]thiopyran-2-yl}butanoic acid,
(22) 2-propanyl 4-{(2S,4aR,5R,6R,7aS)-6-hydroxy-5-[(3R)-3-hydroxy-4-phenoxybutyl]octahydrocyclopenta[b]thiopyran-2-yl}butanoate,
(23) 2-propanyl 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoate,
(24) 2-propanyl 4-{(2S,4aR,5R,6R,7aS)-5-[(1E,3R)-4-(3-chlorophenoxy)-3-hydroxy-1-buten-1-yl]-6-hydroxyoctahydrocyclopenta[h]thiopyran-2-yl}butanoate,
(25) 2-propanyl 4-{(2S,4aR,5R,6R,7aS)-6-hydroxy-5-[(1E,3R)-3-hydroxy-4-(3-methylphenoxy)-1-buten-1-yl]octahydrocyclopenta[b]thiopyran-2-yl}butanoate,
(26) 2-propanyl 4-{(2S,4aR,5R,6R,7aS)-5-[(1E,3R)-4-(3-fluorophenoxy)-3-hydroxy-1-buten-1-yl]-6-hydroxyoctahydrocyclopenta[b]thiopyran-2-yl}butanoate,
(27) 2-propanyl 4-{(2S,4aR,5R,6R,7aS)-5-[(1E,3R)-4-(4-fluorophenoxy)-3-hydroxy-1-buten-1-yl]-6-hydroxyoctahydrocyclopenta[b]thiopyran-2-yl}butanoate,
(28) 2-propanyl 4-{(2S,4aR,5R,6R,7aS)-6-hydroxy-5-[(1E,3R)-3-hydroxy-4-(3-methoxyphenoxy)-1-buten-1-yl]octahydrocyclopenta[b]thiopyran-2-yl}butanoate,
(29) 2-propanyl 4-{(2S,4aR,5R,6R,7aS)-6-hydroxy-5-[(1E,3R)-3-hydroxy-4-(2-methoxyphenoxy)-1-buten-1-yl]octahydrocyclopenta[b]thiopyran-2-yl}butanoate and
(30) 2-propanyl 4-[(2S,4aR,5R,6R,7aS)-6-hydroxy-5-{(1E,3R)-3-hydroxy-4-[3-(trifluoromethyl)phenoxyl-1-buten-1-yl}octahydrocyclopenta[b]thiopyran-2-yl]butanoate;
[5] a pharmaceutical composition comprising the compound represented by the formula (I) according to [1], or a salt thereof, a solvate thereof, or a prodrug thereof;
[6] the pharmaceutical composition according to [5], wherein the compound represented by the formula (I) according to [1], or a salt thereof, a solvate thereof, or a prodrug thereof is an FP agonist;
[7] the pharmaceutical composition according to [5], which is an agent for preventing and/or treating an ocular disease;
[8] the pharmaceutical composition according to [7], wherein the ocular disease is glaucoma, ocular hypertension, macular edema, macular degeneration, retina and optic nerve tensile force rise, myopia, hypermetropia, astigmatism, dry eye, retinal detachment, cataract, intraocular pressure rise due to trauma or inflammation, intraocular pressure rise due to a drug, or intraocular pressure rise after operation;

[9] an agent for preventing and/or treating an ocular disease, comprising a compound represented by the formula (II);

[Chemical formula 17]

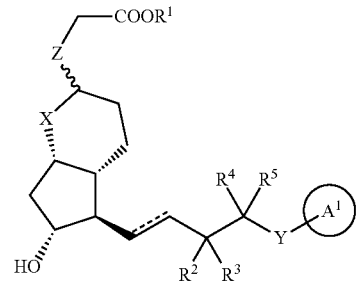

(II)

(wherein X represents (1) —O— or (2) —S—; a ring $A^1$ represents a C3-10 carbocyclic ring optionally substituted with 1 to 5 substituents selected from the group consisting of (1) a halogen atom, (2) $CF_3$, (3) $OCF_3$, (4) a C1-4 alkoxy group, (5) a C1-4 alkyl group, (6) a hydroxyl group and (7) a nitrile group, or a 3- to 10-membered heterocyclic ring optionally substituted with 1 to 5 substituents selected from the group consisting of (1) a halogen atom, (2) $CF_3$, (3) $OCF_3$, (4) a C1-4 alkoxy group, (5) a C1-4 alkyl group, (6) a hydroxyl group and (7) a nitrile group; $R^2$, $R^3$, $R^4$ and $R^5$ each independently represent (1) a hydrogen atom, (2) a C1-4 alkyl group, (3) a halogen atom or (4) a hydroxyl group, and other symbols represent the same meanings as those described in [1]), or a salt thereof, a solvate thereof, or a prodrug thereof;
[10] a method of preventing and/or treating an ocular disease, comprising administering an effective amount of the compound represented by the formula (I) according to [1], or a salt thereof, a solvate thereof, or a prodrug thereof to a mammal; and
[11] the compound represented by the formula (I) according to [1], or a salt thereof, a solvate thereof, or a prodrug thereof, which is used for preventing and/or treating an ocular disease; etc.

Effects of the Invention

The present invention compound has strong intraocular pressure lowering action, and is useful as a therapeutic agent for glaucoma having no side effect on eyes such as ocular stimulating property (hyperemia, cloudy cornea etc.), humor protein rise etc.

MODE FOR CARRYING OUT THE INVENTION

Figure 1:
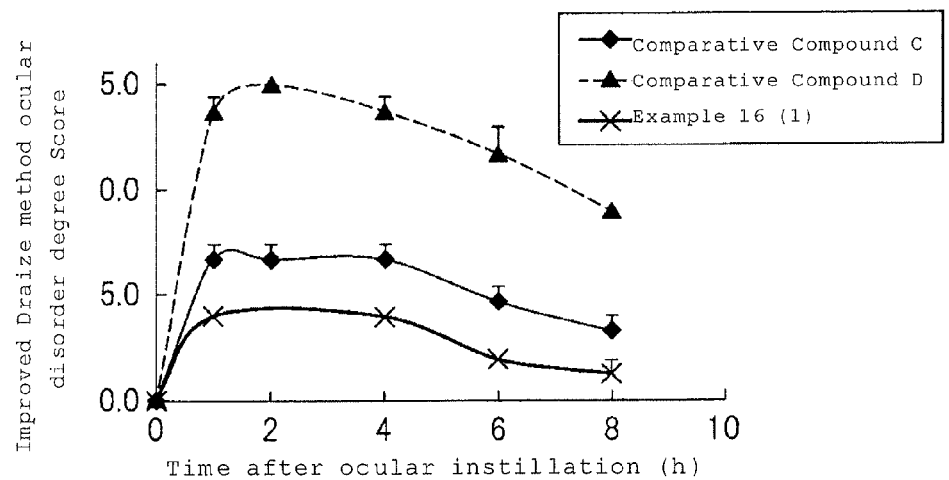
FIG. 1A graph expressing transition of ocular stimulating property based on the Draize score after ocular instillation of the present invention compound and a comparative compound.

The present invention will be explained in detail below.
In the present invention, the C1-6 alkyl group means a straight or branched C1-6 alkyl group such as methyl, ethyl, propyl, isopropyl, butyl, sec-butyl, tert-butyl, pentyl, isopentyl, tert-pentyl, neopentyl, hexyl etc.
In the present invention, the C1-4 alkyl group means a straight or branched C1-4 alkyl group such as methyl, ethyl, propyl, isopropyl, butyl, sec-butyl, tert-butyl etc.

In the present invention, the C1-4 alkoxy group means a straight or branched C1-4 alkoxy group such as methoxy, ethoxy, propoxy, isopropoxy, butoxy, isobutyloxy, tert-butoxy etc.

In the present invention, the halogen atom means fluorine, chlorine, bromine, and iodine.

In the present invention, the C3-10 carbocyclic ring means a C3-10 monocyclic or bicyclic carbocyclic ring, or a part or all of which may be saturated, and examples include cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, perhydroindane, naphthalene, dihydronaphthalene, tetrahydronaphthalene, perhydronaphthalene etc.

In the present invention, the C3-7 carbocyclic ring means a C3-7 monocyclic carbocyclic ring, or a part or all of which may be saturated, and examples include cyclopropane, cyclobutane, cyclopentane, cyclohexane, cycloheptane, cyclooctane, cyclopentene, cyclohexene, cycloheptene, cyclopentadiene, cyclohexadiene, cycloheptadiene, benzene, etc.

In the present invention, the 3- to 10-membered heterocyclic ring means a 3- to 10-membered monocyclic or bicyclic heterocyclic ring, a part or all of which may be saturated, comprising 1 to 5 hetero atoms selected from an oxygen atom, a nitrogen atom and a sulfur atom, and examples include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isooxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, pyrrolopyridine, benzoxazole, benzothiazole, benzimidazole, chromene, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, and perhydrobenzimidazole.

In the present invention, the sulfur atom in Z includes a sulfur atom which may be oxidized. The sulfur atom which may be oxidized means S, SO or $SO_2$.

In the present invention, as $R^1$, methyl, ethyl, propyl, or isopropyl is preferable.

In the present invention, as Z, —$(CH_2)_m$— is preferable.
In the present invention, as Y, —O— is preferable.
In the present invention, as X, —S— is preferable.
In the present invention, the substituent of the benzene ring represented by the ring A is preferably a C1-4 alkyl group, a C1-4 alkoxy group, $CF_3$ or a halogen atom, and it is also preferable that the benzene ring is unsubstituted.

In the present invention, as m, the integer of 2 is preferable.
In the present invention, the α chain means a side chain binding to a 6-membered ring, and the ω chain means a side chain binding to a 5-membered ring, in each formula.

In the present invention, among the compounds represented by the formula (I), a compound represented by the formula (I-1):

[Chemical formula 18]

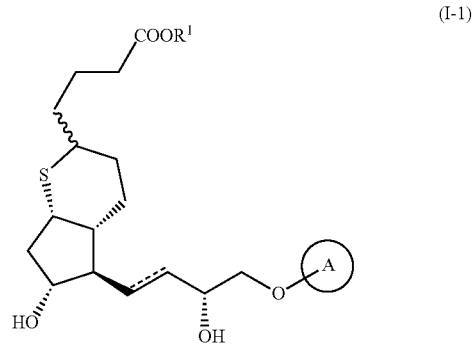

(I-1)

(wherein all symbols represent the same meanings as those described above) is preferable.

In the present invention, the compound represented by the formula (I-1) is preferably, for example,
(1) methyl 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoate (compound 14),
(2) methyl 4-{(2R,4aR,5R,6R,7aS)-6-hydroxy-5-[(1E,3R)-3-hydroxy-4-phenoxy-1-buten-1-yl]octahydrocyclopenta[b]thiopyran-2-yl}butanoate (compound 14 (3)), (3) 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoic acid (compound 15), (4) 4-{(2S,4aR,5R,6R,7aS)-6-hydroxy-5-[(1E,3S)-3-hydroxy-5-phenyl-1-penten-1-yl]octahydrocyclopenta[b]thiopyran-2-yl}butanoic acid (compound 15 (2)), (5) 4-{(2R,4aR,5R,6R,7aS)-6-hydroxy-5-[(1E,3R)-3-hydroxy-4-phenoxy-1-buten-1-yl]octahydrocyclopenta[b]thiopyran-2-yl}butanoic acid (compound 15 (3)), (6) 4-{(2S,4aR,5R,6R,7aS)-5-[(1E,3R)-4-(4-fluorophenoxy)-3-hydroxy-1-buten-1-yl]-6-hydroxyoctahydrocyclopenta[b]thiopyran-2-yl}butanoic acid (compound 15 (4)), (7) 4-{(2S,4aR,5R,6R,7aS)-5-[(1E,3R)-4-(3-chlorophenoxy)-3-hydroxy-1-buten-1-yl]-6-hydroxyoctahydrocyclopenta[b]thiopyran-2-yl}butanoic acid (compound 15 (5)), (8) 4-{(2S,4aR,5R,6R,7aS)-6-hydroxy-5-[(1E,3R)-3-hydroxy-4-(3-methylphenoxy)-1-buten-1-yl]octahydrocyclopenta[b]thiopyran-2-yl}butanoic acid (compound 15 (6)), (9) 4-{(2S,4aR,5R,6R,7aS)-5-[(1E,3R)-4-(2-fluorophenoxy)-3-hydroxy-1-buten-1-yl]-6-hydroxyoctahydrocyclopenta[b]thiopyran-2-yl}butanoic acid (compound 15 (7)),

(10) 4-{(2S,4aR,5R,6R,7aS)-5-[(1E,3R)-4-(3-fluorophenoxy)-3-hydroxy-1-buten-1-yl]-6-hydroxyoctahydrocyclopenta[b]thiopyran-2-yl}butanoic acid (compound 15 (8)),

(11) 4-[(2S,4aR,5R,6R,7aS)-6-hydroxy-5-{(1E,3R)-3-hydroxy-4-[3-(trifluoromethyl)phenoxy]-1-buten-1-yl}octahydrocyclopenta[b]thiopyran-2-yl]butanoic acid (compound 15 (9)),

(12) 4-{(2S,4aR,5R,6R,7aS)-6-hydroxy-5-[(1E,3R)-3-hydroxy-4-(2-methoxyphenoxy)-1-buten-1-yl]octahydrocyclopenta[b]thiopyran-2-yl}butanoic acid (compound 15 (10)),

(13) 4-{(2S,4aR,5R,6R,7aS)-6-hydroxy-5-[(1E,3R)-3-hydroxy-4-(3-methoxyphenoxy)-1-buten-1-yl]octahydrocyclopenta[b]thiopyran-2-yl}butanoic acid (compound 15 (11)),

(14) 4-{(2S,4aR,5R,6R,7aS)-6-hydroxy-5-[(1E,3R)-3-hydroxy-4-(4-methoxyphenoxy)-1-buten-1-yl]octahydrocyclopenta[b]thiopyran-2-yl}butanoic acid (compound 15 (12)),

(15) 4-{(2S,4aR,5R,6R,7aS)-6-hydroxy-5-[(1E,3R)-3-hydroxy-4-(2-methylphenoxy)-1-buten-1-yl]octahydrocyclopenta[b]thiopyran-2-yl}butanoic acid (compound 15 (13)),

(16) 4-{(2S,4aR,5R,6R,7aS)-6-hydroxy-5-[(1E,3R)-3-hydroxy-4-(4-methylphenoxy)-1-buten-1-yl]octahydrocyclopenta[b]thiopyran-2-yl}butanoic acid (compound 15 (14)),

(17) 4-{(2S,4aR,5R,6R,7aS)-5-[(1E,3R)-4-(4-chlorophenoxy)-3-hydroxy-1-buten-1-yl]-6-hydroxyoctahydrocyclopenta[b]thiopyran-2-yl}butanoic acid (compound 15 (15)),

(18) 4-{(2S,4aR,5R,6R,7aS)-5-[(1E,3R)-4-(2-chlorophenoxy)-3-hydroxy-1-buten-1-yl]-6-hydroxyoctahydrocyclopenta[b]thiopyran-2-yl}butanoic acid (compound 15 (16)),

(19) 4-[(2S,4aR,5R,6R,7aS)-6-hydroxy-5-{(1E,3R)-3-hydroxy-4-[2-(trifluoromethyl)phenoxyl]-1-buten-1-yl}octahydrocyclopenta[b]thiopyran-2-yl butanoic acid (compound 15 (17)),

(20) 4-[(2S,4aR,5R,6R,7aS)-6-hydroxy-5-{(1E,3R)-3-hydroxy-4-[4-(trifluoromethyl)phenoxy]-1-buten-1-yl}octahydrocyclopenta[b]thiopyran-2-yl]butanoic acid (compound 15 (18)),

(21) 4-{(2S,4aR,5R,6R,7aS)-6-hydroxy-5-[(3R)-3-hydroxy-4-phenoxybutyl]octahydrocyclopenta[b]thiopyran-2-yl}butanoic acid (compound 15 (20)),

(22) 2-propanyl 4-{(2S,4aR,5R,6R,7aS)-6-hydroxy-5-[(3R)-3-hydroxy-4-phenoxybutyl]octahydrocyclopenta[b]thiopyran-2-yl}butanoate (compound 16),

(23) 2-propanyl 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoate (compound 16 (1)),

(24) 2-propanyl 4-{(2S,4aR,5R,6R,7aS)-5-[(1E,3R)-4-(3-chlorophenoxy)-3-hydroxy-1-buten-1-yl]-6-hydroxyoctahydrocyclopenta[b]thiopyran-2-yl}butanoate (compound 16 (2)),

(25) 2-propanyl 4-{(2S,4aR,5R,6R,7aS)-6-hydroxy-5-[(1E,3R)-3-hydroxy-4-(3-methylphenoxy)-1-buten-1-yl]octahydrocyclopenta[b]thiopyran-2-yl}butanoate (compound 16 (3)),

(26) 2-propanyl 4-{(2S,4aR,5R,6R,7aS)-5-[(1E,3R)-4-(3-fluorophenoxy)-3-hydroxy-1-buten-1-yl]-6-hydroxyoctahydrocyclopenta[b]thiopyran-2-yl}butanoate (compound 16 (4)),

(27) 2-propanyl 4-{(2S,4aR,5R,6R,7aS)-5-[(1E,3R)-4-(4-fluorophenoxy)-3-hydroxy-1-buten-1-yl]-6-hydroxyoctahydrocyclopenta[b]thiopyran-2-yl}butanoate (compound 16 (5)),

(28) 2-propanyl 4-{(2S,4aR,5R,6R,7aS)-6-hydroxy-5-[(1E,3R)-3-hydroxy-4-(3-methoxyphenoxy)-1-buten-1-yl]octahydrocyclopenta[b]thiopyran-2-yl}butanoate (compound 16 (6)),

(29) 2-propanyl 4-{(2S,4aR,5R,6R,7aS)-6-hydroxy-5-[(1E,3R)-3-hydroxy-4-(2-methoxyphenoxy)-1-buten-1-yl]octahydrocyclopenta[b]thiopyran-2-yl}butanoate (compound 16 (7)) or

(30) 2-propanyl 4-[(2S,4aR,5R,6R,7aS)-6-hydroxy-5-{(1E,3R)-3-hydroxy-4-[3-(trifluoromethyl)phenoxy]-1-buten-1-yl}octahydrocyclopenta[b]thiopyran-2-yl]butanoate (compound 16 (9)) etc.

More preferable is (1) methyl 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoate (compound 14), (2) 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoic acid (compound 15) or (3) 2-propanyl 4-{(2S,4aR,5R,6R,7aS)-6-hydroxy-5-[(1E, 3R)-3-hydroxy-4-phenoxy-1-buten-1-yl]octahydrocyclopenta[b]thiopyran-2-yl}butanoate (compound 16 (1)).

[Isomer]

In the present invention, an isomer includes all isomers unless otherwise is indicated. For example, the alkyl group includes a straight alkyl group and a branched alkyl group. Further, all of an isomer at a double bond, a ring, or a condensed ring (E isomer, Z isomer, cis isomer, trans isomer), an isomer due to the presence of an asymmetric carbon etc. (R, S isomer, a, p configuration, enantiomer, diastereomer), an optically active body having optical rotation (D, L, d, l isomer), a polar body derived from chromatographic separation (high polar compound, low polar compound), an equilibrated compound, a rotation isomer, a mixture of them at an arbitrary ratio, and a racemic mixture are included in the present invention. In addition, in the present invention, the isomer includes all isomers derived from tautomers.

In addition, the optically active compound in the present invention may include not only 100% pure compounds, but also other optical isomers which are less than 50% pure.

In the present invention, unless otherwise is indicated, as is apparent to a person skilled in the art, a symbol:

[Chemical formula 19]

represents that a group is bound to another side of a paper plane (i.e. α configuration),

[Chemical formula 20]

represents that a group is bound to a front side of a paper plane (i.e. β configuration),

[Chemical formula 21]

represents α configuration, β configuration or a mixture thereof, and

[Chemical formula 22]

represents a mixture of α configuration and β configuration.

The compound represented by the formula (I) is converted into a corresponding salt by the known method. As the salt, a water-soluble salt is preferable. Examples of the suitable salt include salts of an alkali metal (potassium, sodium etc.), salts of an alkaline earth metal (calcium, magnesium etc.), ammonium salts, salts of pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.), acid addition salts (inorganic acid salts (hydrochloride, hydrobromide, hydroiodide, sulfate, phosphate, nitrate etc.), organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate etc.) etc.

The compound represented by the formula (I) and a salt thereof can be also converted into a solvate. It is preferable that the solvate is low-toxic and water-soluble. Examples of a suitable solvate include solvates with, for example, water, or alcohol-based solvents (e.g. ethanol etc.).

In addition, a prodrug of the compound represented by the formula (I) refers to a compound which is converted into the compound represented by the formula (I) by a reaction with an enzyme or gastric acid in a living body. Examples of the prodrug of the compound represented by the formula (I), when the compound represented by the formula (I) has a hydroxyl group, include compounds in which a hydroxyl group is acylated, alkylated, phosphorylated, or boronized (e.g. compounds in which a hydroxyl group of the present invention compound is acetylated, palmitoylated, propanoylated, pivaloylated, succinylated, fumarylated, alanylated, or dimethylaminomethylcarbonized etc.); compounds in which a carboxyl group of the compound represented by the formula (I) is esterified, or amidated (examples; compounds in which a carboxyl group of the compound represented by the formula (I) is ethyl-esterified, isopropyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated) etc. These compounds can be produced by the known method. In addition, the prodrug of the compound represented by the formula (I) may be any of a hydrate and a non-hydrate. In addition, the prodrug of the compound represented by the formula (I) may be a prodrug which is changed to the compound represented by the formula (I) under the physiological condition, as described in "Development of Medicaments" published in 1990 by Hirokawa-Shoten Ltd., Vol. 7, "Molecular Design", p. 163-198. Further, the compound represented by the formula (I) may be labeled with an isotopic element (e.g. $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$ etc.) etc.

Particularly, examples of a preferable prodrug of the compound represented by the formula (I), upon ocular instillation administration of the compound represented by the formula (I), include compounds in which a carboxyl group possessed by the compound represented by the formula (I) is methyl-esterified, ethyl-esterified, propyl-esterified, isopropyl-esterified, butyl-esterified, isobutyl-esterified, sec-butyl-esterified, tert-butyl-esterified, pentyl-esterified, isopentyl-esterified, neopentyl-esterified, cyclopentyl-esterified, hexyl-esterified, cyclohexyl-esterified, trifluoroethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated etc.

[Process for Producing Present Invention Compound]

The present invention compound can be produced by the known method, for example, the method described in Comprehensive Organic Transformations: A Guide to Functional Group Preparations 2nd Edition (Richard C. Larock, John Wiley & Sons Inc, 1999), or can be produced by appropriately improving the methods shown in Examples, and using a combination of them. For example, a compound having —S— as X in the formula (II) can be produced using the method described in U.S. Pat. No. 4,367,237, and a compound having —O— as X in the formula (II) can be produced using the method described in U.S. Pat. No. 4,490,537.

The compound represented by the formula (I) can be produced by the following method.

Among the compounds represented by the formula (I), a compound in which

[Chemical formula 23]

represents a double bond, i.e. a compound represented by the formula (I-a):

[Chemical formula 24]

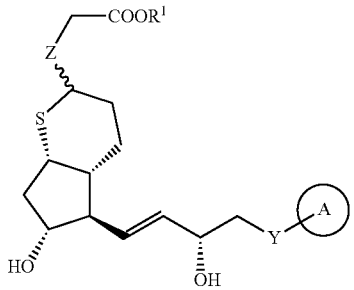

(I-a)

(wherein all symbols represent the same meanings as those described above) can be produced by the following reaction step formula 1.

<Reaction step formula 1>

[Chemical formula 25]

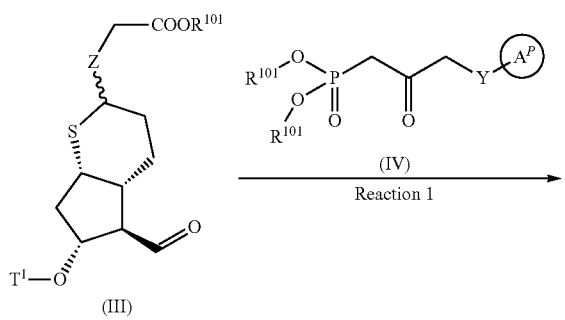

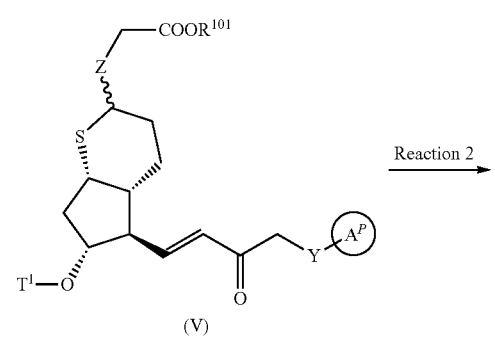

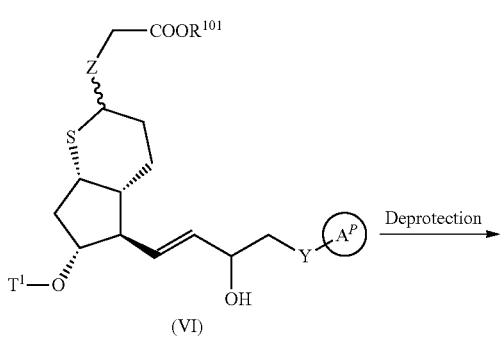

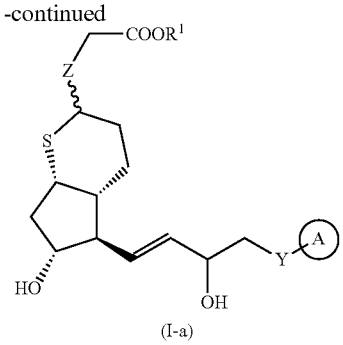

(I-a)

(wherein $R^{101}$ represents a C1-6 alkyl group, and $T^1$ represents a protective group of a hydroxyl group (e.g. 2-tetrahydropyranyl (THP) group etc.); a ring $A^P$ represents the same meaning as that of the ring A, but when the ring A has a substituent, the substituent is protected if protection is needed; other symbols represent the same meanings as those described above)

In the reaction step formula 1, the reaction 1 is known and is performed by, for example, reacting a compound represented by the formula (III) and a compound represented by the formula (IV) at a temperature of −20 to 70° C. in an organic solvent (e.g. tetrahydrofuran, dimethylformamide, dioxane, acetonitrile, ethanol etc.) or in water, or in a mixed solution thereof, in the presence of a base (e.g. sodium hydride, potassium tert-butoxide, potassium carbonate, tertiary amine+lithium chloride etc.).

In the reaction step formula 1, the reaction 2 is known, and is performed by reacting a compound represented by the formula (V), which is obtained in the reaction 1, at a temperature of −20 to 50° C. in an organic solvent (tetrahydrofuran, methanol, dimethoxyethane, toluene, dichloromethane, diethyl ether, dioxane etc.), in the presence or absence of cerium chloride using a reducing agent (sodium borohydride, zinc borohydride etc.). When only one of steric isomers is obtained, the reaction is performed at a temperature of −100 to 50° C. using an asymmetric reducing agent (chlorodiisopinocamphenylborane etc.), or a combination of an asymmetric aid and a reducing agent ((R)-2-methyl-CBS-oxazaborolidine and boron hydride•tetrahydrofuran complex, (S)-(−)-binaphthol and lithium aluminum hydride etc.).

In the reaction step formula 1, a reaction of deprotecting a protective group is known, and can be performed by the following step. Examples include (1) a deprotection reaction by alkali hydrolysis, (2) a deprotection reaction under the acidic condition, (3) a deprotection reaction by hydrogenation degradation, (4) a deprotection reaction of a silyl group, (5) a deprotection reaction using a metal, (6) a deprotection reaction using a metal complex etc.

To specifically explain these methods, (1) the deprotection reaction by alkali hydrolysis is performed, for example, at 0 to 40° C. in an organic solvent (e.g. methanol, tetrahydrofuran, dioxane etc.), using a hydroxide of an alkali metal (e.g. sodium hydroxide, potassium hydroxide, lithium hydroxide etc.), a hydroxide of an alkaline earth metal (e.g. barium hydroxide, calcium hydroxide etc.), or carbonate (e.g. sodium carbonate, potassium carbonate etc.), or an aqueous solution thereof, or a mixture thereof.

(2) The deprotection reaction under the acidic condition is performed, for example, at 0 to 100° C. in an organic solvent (e.g. dichloromethane, chloroform, dioxane, ethyl acetate, methanol, isopropyl alcohol, tetrahydrofuran, anisole etc.), in an organic acid (e.g. acetic acid, trifluoroacetic acid, methanesulfonic acid, p-tosylate etc.), or an inorganic acid (e.g. hydrochloric acid, sulfuric acid etc.) or a mixture thereof (e.g. hydrogen bromide/acetic acid etc.), in the presence or absence of 2,2,2-trifluoroethanol.

(3) The deprotection reaction by hydrogenation degradation is performed, for example, at 0 to 200° C. in a solvent (e.g. ether-based solvent (e.g. tetrahydrofuran, dioxane, dimethoxyethane, diethyl ether etc.), alcohol-based solvent (e.g. methanol, ethanol etc.), benzene-based solvent (e.g. benzene, toluene etc.), ketone-based solvent (e.g. acetone, methyl ethyl ketone etc.), nitrile-based solvent (e.g. acetonitrile etc.), amide-based solvent (e.g. N,N-dimethylformamide etc.), water, ethyl acetate, acetic acid, or a mixed solvent of two or more of them etc.), in the presence of a catalyst (e.g. palladium-carbon, palladium black, palladium hydroxide-carbon, platinum oxide, Raney nickel etc.) under the hydrogen atmosphere at normal pressure or under pressure, or in the presence of ammonium formate.

(4) The deprotection reaction of a silyl group is performed, for example, at 0 to 40° C. in an organic solvent which is miscible with water (e.g. tetrahydrofuran, acetonitrile etc.) using tetrabutylammonium fluoride. Alternatively, the reaction is performed, for example, at −10 to 100° C. in an organic acid (e.g. acetic acid, trifluoroacetic acid, methanesulfonic acid, p-tosylate etc.), or an inorganic acid (e.g. hydrochloric acid, sulfuric acid etc.) or a mixture thereof (e.g. hydrogen bromide/acetic acid etc.).

(5) The deprotection reaction using a metal is performed, for example, at 0 to 40° C. in an acidic solvent (e.g. acetic acid, a buffer of pH 4.2 to 7.2, or a mixed solution of any of those solutions and an organic solvent such as tetrahydrofuran etc.) in the presence of a zinc powder, if necessary, while an ultrasound is applied.

(6) The deprotection reaction using a metal complex is performed, for example, at 0 to 40° C. in an organic solvent (e.g. dichloromethane, N,N-dimethylformamide, tetrahydrofuran, ethyl acetate, acetonitrile, dioxane, ethanol etc.), water or a mixed solvent thereof, in the presence of a trap reagent (e.g. tributyltin hydride, triethylsilane, dimedone, morpholine, diethylamine, pyrrolidine etc.), an organic acid (e.g. acetic acid, formic acid, 2-ethylhexanoic acid etc.) and/or an organic acid salt (e.g. sodium 2-ethylhexanoate, potassium 2-ethylhexanoate etc.), in the presence or absence of a phosphine-based reagent (e.g. triphenylphosphine etc.), using a metal complex (e.g. tetrakistriphenylphosphinepalladium (0), bis(triphenylphosphine)palladium (II) dichloride, palladium (II) acetate, tris(triphenylphosphine)rhodium (I) chloride etc.).

Additionally, in addition to the above reactions, the deprotection reaction can be performed, for example, by the method described in T. W. Greene, Protective Groups in Organic Synthesis, Wiley, New York, 1999.

Examples of the protective group of a hydroxyl group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group and a 2,2,2-trichloroethoxycarbonyl (Troc) group etc.

Examples of the protective group of an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl (SEM) group etc.

The protective group of a hydroxyl group is not particularly limited, as far as it is a group which can be easily and selectively left, in addition to the aforementioned protective groups. Protective groups described in, for example, T. W. Greene, Protective Groups in Organic Synthesis, Wiley, New York, 1999 are used.

The compound represented by the formula (III) can be produced by the following reaction step formula 2.

<Reaction step formula 2>

[Chemical formula 26]

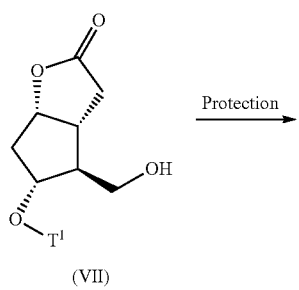

(VII)

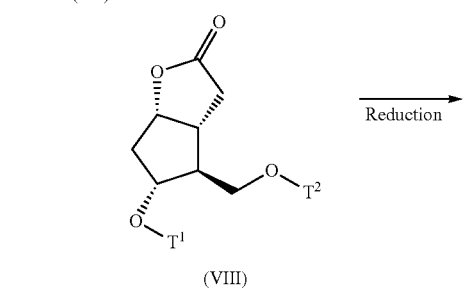

(VIII)

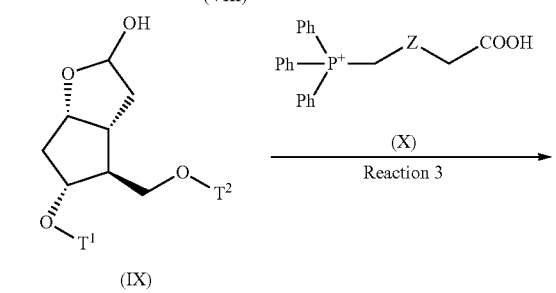

(IX)

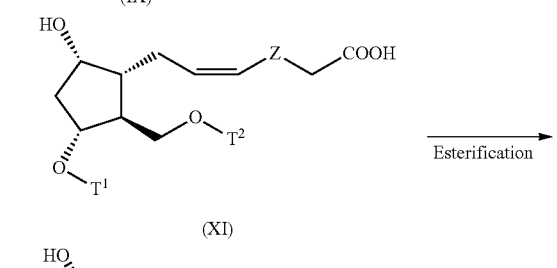

(XI)

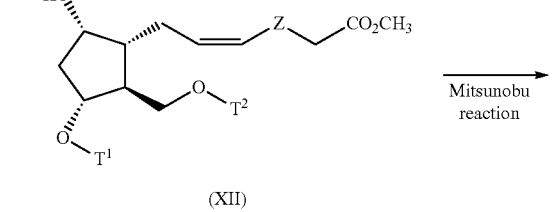

(XII)

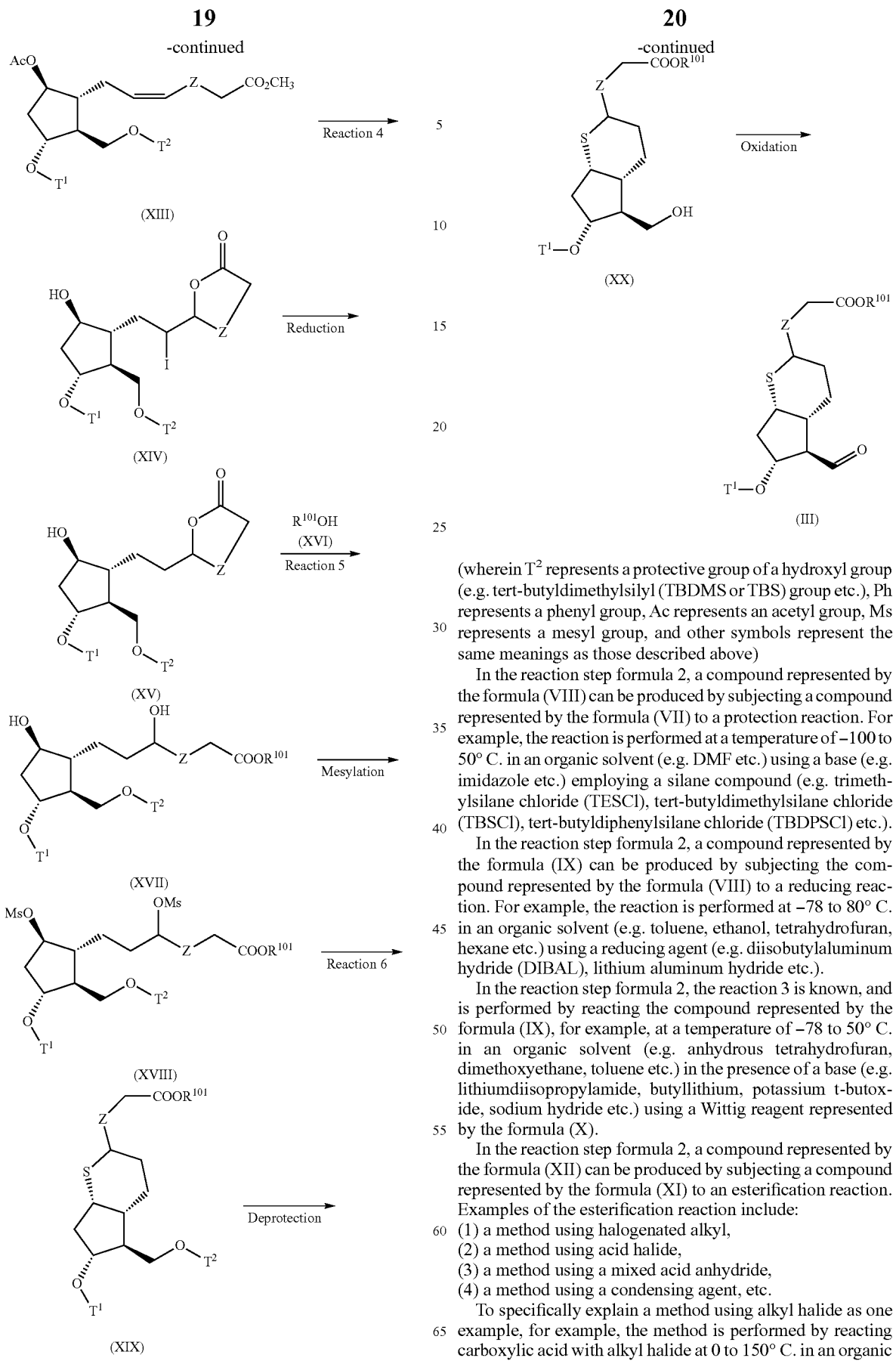

(wherein $T^2$ represents a protective group of a hydroxyl group (e.g. tert-butyldimethylsilyl (TBDMS or TBS) group etc.), Ph represents a phenyl group, Ac represents an acetyl group, Ms represents a mesyl group, and other symbols represent the same meanings as those described above)

In the reaction step formula 2, a compound represented by the formula (VIII) can be produced by subjecting a compound represented by the formula (VII) to a protection reaction. For example, the reaction is performed at a temperature of −100 to 50° C. in an organic solvent (e.g. DMF etc.) using a base (e.g. imidazole etc.) employing a silane compound (e.g. trimethylsilane chloride (TESCl), tert-butyldimethylsilane chloride (TBSCl), tert-butyldiphenylsilane chloride (TBDPSCl) etc.).

In the reaction step formula 2, a compound represented by the formula (IX) can be produced by subjecting the compound represented by the formula (VIII) to a reducing reaction. For example, the reaction is performed at −78 to 80° C. in an organic solvent (e.g. toluene, ethanol, tetrahydrofuran, hexane etc.) using a reducing agent (e.g. diisobutylaluminum hydride (DIBAL), lithium aluminum hydride etc.).

In the reaction step formula 2, the reaction 3 is known, and is performed by reacting the compound represented by the formula (IX), for example, at a temperature of −78 to 50° C. in an organic solvent (e.g. anhydrous tetrahydrofuran, dimethoxyethane, toluene etc.) in the presence of a base (e.g. lithiumdiisopropylamide, butyllithium, potassium t-butoxide, sodium hydride etc.) using a Wittig reagent represented by the formula (X).

In the reaction step formula 2, a compound represented by the formula (XII) can be produced by subjecting a compound represented by the formula (XI) to an esterification reaction. Examples of the esterification reaction include:
(1) a method using halogenated alkyl,
(2) a method using acid halide,
(3) a method using a mixed acid anhydride,
(4) a method using a condensing agent, etc.

To specifically explain a method using alkyl halide as one example, for example, the method is performed by reacting carboxylic acid with alkyl halide at 0 to 150° C. in an organic solvent (e.g. acetonitrile, acetone, N,N-dimethylformamide, dimethyl sulfoxide, chloroform, dichloromethane, diethyl ether, tetrahydrofuran etc.) in the presence of carbonate (e.g. cesium carbonate, sodium carbonate, potassium carbonate etc.), an organic base (e.g. dimethylformamide, triethylamine, diisopropylethylamine etc.) or hydride of an alkyl metal (sodium hydride etc.).

In the reaction step formula 2, a compound represented by the formula (XIII) can be produced by subjecting the compound represented by the formula (XII) to a Mitsunobu reaction. The Mitsunobu reaction is known, and is performed by, for example, reacting an alcohol with a carboxylic acid (formic acid, acetic acid, benzoic acid etc.) at 0 to 60° C. in an organic solvent (dichloromethane, diethyl ether, tetrahydrofuran, acetonitrile, benzene, toluene etc.) in the presence of an azo compound (diethyl azodicarboxylate (DEAD), diisopropyl azodicarboxylate, 1,1'-(azodicarbonyl)dipiperidine, 1,1'-azobis(N,N-dimethylformamide) etc.) and a phosphine compound (triphenylphosphine, tributylphosphine, trimethylphosphine, polymer support triphenylphosphine etc.).

In the reaction step formula 2, the reaction 4 is known, and is performed by reacting the compound represented by the formula (XIII), for example, at a temperature of −30 to 100° C. in an organic solvent (methanol, ethanol, acetonitrile, N,N-dimethylformamide, tetrahydrofuran etc.) or water, or a mixed liquid thereof in the presence or absence of a base (sodium hydroxide, sodium carbonate, sodium hydrogen carbonate etc.) using an iodination reagent (iodine, potassium iodide, N-iodosuccinimide (NIS) etc.).

In the reaction step formula 2, a compound represented by the formula (XV) can be produced by subjecting a compound represented by the formula (XIV) to a reducing reaction in the same manner as described above.

In the reaction step formula 2, the reaction 5 is known, and is performed by reacting the compound represented by the formula (XV), for example, at a temperature of 0 to 100° C. in an alcohol represented by the formula (XVI) using an acid (hydrochloric acid, p-toluenesulfonic acid, iodotrimethylsilane etc.) or a base (sodium methylate, potassium carbonate, triethylamine, etc.).

In the reaction step formula 2, the reaction 6 is known, and is performed by reacting a compound represented by the formula (XVIII), for example, at a temperature of 0 to 100° C. in an organic solvent (methanol, ethanol, acetonitrile, N,N-dimethylformamide, tetrahydrofuran etc.) or water, or a mixed liquid thereof in the presence or absence of a base (sodium methylate, sodium hydroxide, sodium hydrogen carbonate, potassium carbonate etc.) using a sodium hydrosulfide n-hydrate, thioacetic acid, potassium thioacetate etc.

In the reaction step formula 2, a compound represented by the formula (XX) can be produced by subjecting a compound represented by the formula (XIX) to a deprotection reaction in the same manner as described above.

In the reaction step formula 2, the compound represented by the formula (III) can be produced by subjecting the compound represented by the formula (XX) to an oxidation reaction. Examples of the oxidation reaction include:
(1) a method using DMSO oxidation (e.g. Swern oxidation),
(2) a method using a Dess-Martin reagent,
(3) a method using a TEMPO reagent, etc.

To specifically explain the method using DMSO oxidation as one example, for example, the method is performed by reacting an alcohol compound in an organic solvent (e.g. chloroform, dichloromethane, ethyl acetate etc.) in the presence of an activating agent (e.g. oxalyl chloride, acetic acid anhydride, pyridine-sulfur trioxide complex etc.), and an oxidizing agent (e.g. dimethyl sulfoxide etc.) and, further, reacting tertiary amine (e.g. triethylamine, N,N-diisopropylethylamine, N-methylmorpholine, N-ethylpiperidine, diazabicyclo[5.4.0]undec-7-ene etc.) at −78 to 40° C.

In each reaction in the present specification, the compound used as a starting raw material, and the compound represented by the formula (IV) or the formula (VII) are known, or can be easily produced by the known method.

In each reaction in the present specification, a reaction accompanying heating can be performed using a water bath, an oil bath, a sand bath or a microwave, as is apparent to a person skilled in the art.

In each reaction in the present specification, a solid phase-supported reagent supported on a high-molecular polymer (e.g. polystyrene, polyacrylamide, polypropylene, polyethylene glycol etc.) may be appropriately used.

In each reaction in the present specification, the reaction product can be purified by a normal purification means, for example, a method such as distillation under normal pressure or under reduced pressure, high performance liquid chromatography using silica gel or magnesium silicate, thin layer chromatography, an ion-exchange resin, a scavenger resin, or column chromatography or washing, recrystallization etc. Purification may be performed for every reaction, or may be performed after completion of some reactions.

[Toxicity]

The present invention compound has very low toxicity, has little, for example, eye stimulating property (hyperemia, corneal clouding etc.), aqueous humor protein rise etc., and can be safely used as a medicament.

[Application to Medicament]

Since the present invention compound and the compound represented by the formula (II)

[Chemical formula 27]

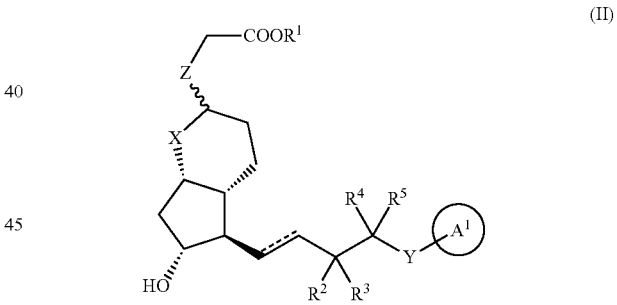

(II)

(wherein all symbols represent the same meanings as those described above), or a salt thereof, a solvate thereof, or a prodrug thereof have selective FP agonist activity, and are useful, based on their intraocular pressure lowering action, as an agent for preventing and/or treating an ocular disease, for example, glaucoma (acute closed-angle glaucoma, chronic closed-angle glaucoma, secondary closed-angle glaucoma, primary open-angle glaucoma, secondary open-angle glaucoma, congenital glaucoma, normal pressure glaucoma, aqueous hyperproduction glaucoma, etc.), ocular hypertension, macular edema, macular degeneration, retina and optic nerve tensile force rise, myopia, hyperopia, astigmatism, dry eye, retinal detachment, cataract, ocular pressure rise due to trauma or inflammation, ocular pressure rise due to a drug such as a steroid or a hormone agent, intraocular pressure rise after operation etc.

In addition, since the present invention compound and the compound represented by the formula (II) have FP agonist activity, they are also useful as a labor inducer, an ecbolic, an oxytocic, a therapeutic agent for dysmenorrhea, a therapeutic agent for osteoporosis, a sunburn revulsant, a white hair preventing agent, a hair growth promoter, an eyelash extender, a therapeutic agent for Meniere's disease, a therapeutic agent for a labyrinthian disease etc.

The present invention compound may be administered as a combination drug, by combining with other drug for
1) complementing and/or potentiating the preventing and/or treating effect of the compound,
2) improving dynamic state•absorption of the compound, decreasing a dose, and/or
3) alleviating side effect of the compound.

The combination drug of the present invention compound and other drug may be administered in a form of a compounding agent in which both ingredients are incorporated into one preparation, or may take a form of administration of separate preparations. When administered by formulating into separate preparations, administration by simultaneous administration and time lag is included. In addition, in administration of time lag, the present invention compound may be administered earlier, and other drug may be administered later, or other drug may be administered earlier, and the present invention compound may be administered later. Respective administration methods may be the same or different.

By combination drug, a disease on which the preventing and/or treating effect is exerted is not particularly limited, but the disease may be a disease on which the preventing and/or treating effect of the preset invention compound is complemented and/or potentiated.

Examples of other drug for complementing and/or potentiating the preventing and/or treating effect on glaucoma of the present invention compound include sympathetic nerve agonists ($\alpha_2$ agonists: e.g. apraclonidine hydrochloride etc., $\beta_2$ agonists: e.g. dipivefrine hydrochloride etc.), parasympathetic nerve agonists (e.g. pilocarpine hydrochloride, carbachol, demecarium, echothiophate and distigmine bromide etc.), sympathetic nerve suppressants ($\alpha_1$ blockers: e.g. bunazosin hydrochloride etc., $\beta$ blockers: e.g. timolol maleate, befunolol hydrochloride, carteolol hydrochloride, and betaxolol hydrochloride etc., $\alpha_1\beta$ blockers: e.g. levobunolol hydrochloride, nipradilol etc.), prostaglandin drugs (e.g. isopropyl unoprostone, latanoprost, bimatoprost, travoprost, tafluprost, EP2 agonist, EP4 agonist and DP agonist etc.), carbonic anhydrase inhibitors (e.g. acetazolamide, diclofenamide, methazolamide, dorzolamide hydrochloride, and brinzolamide etc.), hyperosmotic agents (e.g. glycerin, preparation incorporating glycerin and fructose, isosorbide, and D-mannitol etc.), ROCK (Rho kinase) inhibitors (e.g. Y-27632 etc.), NMDA antagonists etc.

In addition, the therapeutic agent for glaucoma to be combined with the present invention compound includes not only therapeutic agents which have been found out until now, but also therapeutic agents which will be found out from now on.

The present invention compound is usually administered systemically or locally in an oral or parenteral form. Examples of the oral agent include liquid drugs for internal application (e.g. elixirs, syrups, pharmaceutically acceptable water agents, suspensions, emulsions), solid preparations for internal application (e.g. tablets (including sublingual tablets, orally disintegrating tablets), pills, capsules (including hard capsules, soft capsules, gelatin capsules, microcapsules), powders, granules, torches) etc. Examples of the parenteral agents include solutions (e.g. injectables (subcutaneous injectables, intravenous injectables, intramuscular injectables, intraperitoneal injectables, infusions etc.), eye drops (e.g. aqueous eye drops (aqueous eye drops, aqueous suspensions eye drops, viscous eye drops, solubilized eye drops etc.), nonaqueous eye drops (nonaqueous eye drops, nonaqueous suspension eye drops etc.)) etc.), external preparations (e.g. ointment (ocular ointment etc.)), ear drops etc. These preparations may be release-controlled agents such as rapid-releasing preparations and sustained-release preparations. These preparations can be produced by the known method, for example, the method described in Japanese Pharmacopoeia etc.

Solutions for internal application as the oral agent are produced by dissolving, suspending or emulsifying an active ingredient in a diluent which is generally used (e.g. purified water, ethanol or a mixed solution thereof etc.). Further, this solution may contain wetting agents, suspending agents, emulsifiers, sweeteners, flavors, aromatic agents, preservatives, buffers etc.

Solid preparations for internal application as the oral agent are formulated into preparations according to a conventional method by mixing an active ingredient with excipients (e.g. lactose, mannitol, glucose, microcrystalline cellulose, starch etc.), binders (e.g. hydroxypropylcellulose, polyvinylpyrrolidone, magnesium aluminometasilicate etc.), disintegrating agents (e.g. cellulose calcium glycolate etc.), lubricants (e.g. magnesium stearate etc.), stabilizers, solubilizers (glutamic acid, aspartic acid etc.) etc. In addition, if necessary, preparations may be covered with coating agents (e.g. white sugar, gelatin, hydroxypropylcellulose, hydroxypropylmethylcellulose phthalate etc.), or may be covered with two or more layers.

The external preparation as the parenteral agent is produced by the known method, or formulation which is usually used. For example, the ointment preparations are produced by kneading an active ingredient in a base or melting an active ingredient in a base. An ointment base is selected from bases which are known, or are usually used. For example, an ointment base selected from higher fatty acids or higher fatty acid esters (e.g. adipic acid, myristic acid, palmitic acid, stearic acid, oleic acid, adipic acid ester, myristic acid ester, palmitic acid ester, stearic acid ester, oleic acid ester, etc.), waxes (e.g. beewax, whale wax, ceresin etc.), surfactants (e.g. polyoxyethylene alkyl ether phosphoric acid ester etc.), higher alcohols (e.g. cetanol, stearyl alcohol, cetostearyl alcohol etc.), silicone oils (e.g. dimethylpolysiloxane etc.), hydrocarbons (e.g. hydrophilic vaseline, white vaseline, purified lanolin, liquid paraffin etc., glycols (e.g. ethylene glycol, diethylene glycol, propylene glycol, polyethylene glycol, macrogol etc.), vegetable oils (e.g. castor oil, olive oil, sesame oil, turpentine oil etc.), animal oils (e.g. mink oil, yolk oil, squalane, squalene etc.), water, absorption promoter, and rash preventing agents, alone, is used, or a mixture of two or more kinds is used. Further, the ointment base may contain humectants, preservatives, stabilizers, antioxidants, coloring agents etc.

The injectable as the parenteral agent includes solutions, suspensions, emulsions and solid injectables which are used by dissolving or suspending a solid in a solvent upon use. The injectable is used, for example, by dissolving, suspending or emulsifying an active ingredient in a solvent. As the solvent, for example, distilled water for injection, physiological saline, vegetable oil, alcohols such as propylene glycol, polyethylene glycol and ethanol etc., and a combination thereof are used. Further, this injectable may contain stabilizers, solubilizers (e.g. glutamic acid, aspartic acid, polysorbate 80 (registered trademark) etc.), suspending agents, emulsifiers, soothing agents, buffers, preservatives etc. These are produced by sterilization in a final step, or by a sterilization operation method. Alternatively, a sterile solid agent, for example, a lyophilized product is produced, and it can be also used by sterilization before use thereof, or can be also used by dissolving the product in sterile distilled water for injection or other solvent.

Examples of a preferable dosage form of the present invention compound include eye drops, ocular ointments, tablets etc., and more preferable is eye drops or ocular ointment. These can be formulated into preparations using the generally used technique. For example, in the case of eye drops, as additives, tonicity agents, buffers, pH adjusting agents, solubilizers, thickeners, stabilizers, preservatives etc. can be appropriately incorporated. Alternatively, stable eye drops can be also obtained by adding pH adjusting agents, thickeners, or dispersants, and suspending drugs.

Examples of the tonicity agent include glycerin, propylene glycol, sodium chloride, potassium chloride, sorbitol, mannitol, etc.

Examples of the buffer include phosphoric acid, phosphate, citric acid, acetic acid, ϵ-aminocaproic acid etc.

Examples of the pH adjusting agent include hydrochloric acid, citric acid, phosphoric acid, acetic acid, sodium hydroxide, potassium hydroxide, boric acid, borax, sodium carbonate, sodium bicarbonate etc.

Examples of the solubilizer include polysorbate 80, polyoxyethylene hardened castor oil 60, macrogol 4000 etc.

Examples of the thickener and dispersant include cellulose-based polymers such as hydroxypropylmethylcellulose and hydroxypropylcellulose, polyvinyl alcohol, polyvinylpyrrolidone etc., and examples of the stabilizer include edetic acid and sodium edetate etc.

Examples of the preservative (antiseptic agent) include general-use sorbic acid, potassium sorbate, benzalkonium chloride, benzethonium chloride, methyl paraoxybenzoate, propyl paraoxybenzoate, chlorobutanol etc., and these preservatives can be also used by combining them.

In eye drops containing the active ingredient of the present invention, it is desirable that a pH is set at 4.0 to 8.5, and it is desirable that an osmotic pressure ratio is set at around 1.0.

A dose of the active ingredient of the present invention can be appropriately selected depending on a symptom, an age, a dosage form etc. and, in the case of the oral agent, preferably 1 to 100 mg, more preferably 5 to 30 mg may be administered once to a few times (e.g. once to three times) per day. In the case of eye drops, one to a few drops having a concentration of preferably 0.000001 to 5% (w/v), more preferably 0.00001 to 0.05% (w/v) as a one time amount may be administered to eyes once to a few times (e.g. once to eight times) per day. In addition, in the case of the ocular ointment, an ocular ointment having a concentration of preferably 0.000001 to 5% (w/w), more preferably 0.00001 to 0.05% (w/w) may be coated once to a few times (e.g. once to four times) per day.

Of course, since a dose varies depending on a variety of conditions as described above, an amount smaller than the aforementioned dose is sufficient in some cases, or an amount exceeding the range is necessary in some cases.

EXAMPLES

The present invention will be described in detail below by way of Examples, but the present invention is not limited thereto.

A solvent in a parenthesis shown in a place of separation by chromatography and TLC indicates an eluting solvent or a developing solvent used, and a ratio represents a volumetric ratio.

NMR data is data of ¹H-NMR unless otherwise is indicated.

A solvent used in measurement is indicated in a parenthesis shown at a place of NMR.

A compound name used in the present specification is generally named by using a computer program, ACD/Name (registered trademark) or ACD/Name Batch (registered trademark), which performs naming according to the rule of IUPAC, or according to IUPAC nomenclature. For example, a compound represented by

[Chemical formula 28]

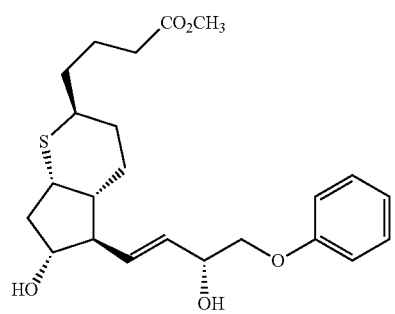

was named as methyl 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoate.

Example 1

(3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-one (compound 1)

To an anhydrous N,N-dimethylformamide (125 mL) solution of (3aR,4S,5R,6aS)-4-(hydroxymethyl)-5-(tetrahydro-2H-pyran-2-yloxy)hexahydro-2H-cyclopenta[b]furan-2-one (CAS registry number: 69222-61-3) (47.5 g) and imidazole (16.3 g) was added dropwise an anhydrous N,N-dimethylformamide (82.5 mL) solution of t-butyldimethylsilyl chloride (30.5 g) in a cold-water bath. The mixture was raised to room temperature and stirred for 2 hours, ethanol (1.25 mL) was then added to the reaction mixture, and the mixture was further stirred for 1 hour. The reaction mixture was poured into ice water (500 mL), hexane (200 mL) and ethyl acetate (100 mL) were added thereto, and the mixture was stirred. The two layers were separated, the organic layer was washed with 1 M hydrochloric acid (100 mL), water (100 mL×two times), a saturated aqueous sodium bicarbonate solution (100 mL) and a saturated saline (100 mL), dried with anhydrous sodium sulfate, and concentrated to obtain a titled compound (68.4 g) having the following physical property values.

TLC: Rf 0.75 (ethyl acetate:hexane=1:4);

NMR (CDCl₃): δ 5.05-4.9 (m, 1H), 4.7-4.6 (m, 1H), 4.25-4.0 (m, 1H), 4.0-3.75 (m, 1H), 3.56 (t, J=7 Hz, 2H), 3.6-3.4 (m, 1H), 2.9-2.0 (m, 6H), 1.9-1.4 (m, 6H), 0.89 (s, 9H), 0.04 (s, 6H).

Example 2

(3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-ol (compound 2)

An anhydrous toluene (315 mL) solution of the compound 1 (68.4 g) was cooled to around −60° C. in a dry ice-methanol bath, and then a diisobutyl aluminum hydride/toluene solution (0.99M, 209 mL) was added dropwise over 33 minutes. The mixture was stirred for 2 hours, and then to the reaction mixture was added dropwise methanol (3.2 mL) at −65° C. over 3 minutes to stop the reaction. The reaction liquid was raised to around 0° C., and water was then added dropwise in two parts (18.5 mL+18 mL) while the mixture was stirred. Thereto was added anhydrous sodium sulfate (7.4 g), and the mixture was stirred at room temperature for 1 hour, and filtered with Celite (trade name). The solid that was filtered off was washed with tetrahydrofuran (160 mL), and concentrated to obtain a titled compound (70.7 g) having the following physical property values.

TLC: Rf 0.60 (ethyl acetate:hexane=1:1);

NMR (CDCl$_3$): δ 5.7-5.35 (m, 1H), 5.3-5.0 (br), 4.8-4.55 (m, 2H), 4.3-3.75 (m, 2H), 3.7-3.3 (m, 2H), 2.7-1.4 (m, 12H), 0.89 (s, 9H), 0.04 (s, 6H).

Example 3

Methyl (5Z)-7-[(1R,2S,3R,5S)-2-({[dimethyl(2-methyl-2-propanyl)silyl]oxy}methyl)-5-hydroxy-3-(tetrahydro-2H-pyran-2-yloxy)cyclopentyl]-5-heptenoate (compound 3)

To an anhydrous tetrahydrofuran (1370 mL) suspension of (4-carboxybutyl)triphenylphosphonium bromide (180.3 g) was added potassium t-butoxide (91.4 g) over 6 minutes while the mixture was stirred on a water bath. The mixture was stirred for 3 hours, and then to the reaction mixture was added dropwise an anhydrous tetrahydrofuran (130 mL) solution of the compound 2 (70.7 g) over 5 minutes. The mixture was further stirred at room temperature for 1 hour, the reaction mixture was then poured into ice water (4.2 L), and a 10% aqueous oxalic dihydrate solution (about 195 mL) was added to adjust pH to 5 to 6. The reaction mixture was extracted (1 L×3 times) with a mixed liquid of hexane (500 mL) and ethyl acetate (500 mL), and the organic layers were combined, and washed with a saturated saline (500 mL). The mixture was dried with anhydrous sodium sulfate, and then concentrated under reduced pressure to obtain a crude product (161.1 g), which was dissolved in acetone (260 mL). To this solution were added potassium carbonate (34.0 g) and methyl iodide (20 mL), and the mixture was stirred at room temperature for 14 hours, and further refluxed for 1 hour. After allowing to cool to room temperature, an insoluble solid was filtered away, and the filtrate was concentrated under reduced pressure to about ½ of the original volume. To this solution was added water (750 mL), and the mixture was extracted with a mixed liquid of hexane (250 mL) and ethyl acetate (250 mL). The extract was washed with a saturated saline (500 mL), and washing water and the aqueous layer were combined, and extracted again with ethyl acetate (200 mL). The organic layers were combined, dried with anhydrous sodium sulfate, and concentrated. The residue was purified by silica gel column chromatography (hexane:ethyl acetate=4:1→1:1) to obtain a titled compound (79.6 g) having the following physical property values.

TLC: Rf 0.76 (ethyl acetate:hexane=1:1);

NMR (CDCl$_3$): δ 5.6-5.3 (m, 2H), 4.7-4.65 (m, 1H), 4.25-4.2 (m, 1H), 4.15-4.05 (m, 1H), 3.95-3.3 (m, 7H), 2.4-1.4 (m, 19H), 0.90 (s, 9H), 0.05 (s, 6H).

Example 4

Methyl (5Z)-7-[(1R,2S,3R,5R)-5-acetoxy-2-({[dimethyl(2-methyl-2-propanyl)silyl]oxy}methyl)-3-(tetrahydro-2H-pyran-2-yloxy)cyclopentyl]-5-heptenoate (compound 4)

An anhydrous tetrahydrofuran (482 mL) solution of the compound 3 (79.6 g) and triphenylphosphine (57.6 g) was cooled to around −40° C. in a dry ice-methanol bath. To this solution was added acetic acid (12.6 mL), and a 40% diethyl azodicarboxylate/toluene solution (100 mL) was then added dropwise over 15 minutes. The mixture was stirred at room temperature for 4.5 hours, the reaction mixture was then poured into water (1600 mL), a mixed solution of hexane (550 mL) and ethyl acetate (550 mL) was added, and the mixture was stirred. The two layers were separated, and the organic layer was then washed with water (540 mL) and a saturated saline (540 mL), dried with anhydrous sodium sulfate, and concentrated. The resulting residue was purified by silica gel column chromatography (hexane:ethyl acetate=10:1) to obtain a titled compound (69.7 g) having the following physical property values.

TLC: Rf 0.70 (ethyl acetate:hexane=1:4);

NMR (CDCl$_3$): δ 7.4-7.1 (m, 4H), 6.0-5.8 (m, 1H), 5.78 (dd, J=16, 6 Hz, 1H), 5.53 (dd, J=16, 8 Hz, 1H), 5.4-5.25 (m, 2H), 4.7-4.6 (m, 4H), 4.5-4.4 (m, 3H), 4.0-3.85 (m, 1H), 3.42 (s, 3H), 3.0-2.8 (m, 2H), 2.72 (dd, J=19, 10 Hz, 1H), 2.65-2.5 (m, 6H), 2.4-2.1 (m, 4H), 2.0-1.6 (m, 5H).

Example 5

(6R)-6-{2-[(1R,2S,3R,5R)-2-({[dimethyl(2-methyl-2-propanyl)silyl]oxy}methyl)-5-hydroxy-3-(tetrahydro-2H-pyran-2-yloxy)cyclopentyl]-1-iodoethyl}tetrahydro-2H-pyran-2-one (high polar compound: compound 5a)

(6S)-6-{2-[(1R,2S,3R,5R)-2-({[dimethyl(2-methyl-2-propanyl)silyl]oxy}methyl)-5-hydroxy-3-(tetrahydro-2H-pyran-2-yloxy)cyclopentyl]-1-iodoethyl}tetrahydro-2H-pyran-2-one (low polar compound: compound 5b)

To a tetrahydrofuran (140 mL) solution of the compound 4 (34.9 g) was added a 2M aqueous sodium hydroxide solution (140 mL), and the mixture was stirred at room temperature for 18 hours and then at 50° C. for 3 hours. The mixture was cooled to −4° C. in an ice-methanol bath, and to the reaction mixture was then added dropwise 2 M hydrochloric acid (111 mL) over 12 minutes while the mixture was kept at 2° C. or lower (pH 5 to 6). The cooling bath was changed to an ice bath, and to the reaction mixture were added sodium hydrogen carbonate (28.5 g) and iodine (17.5 g), and the mixture was stirred. After 2 hours, iodine (34.2 g) was added, the mixture was further stirred for 2.5 hours, and a 5% aqueous sodium thiosulfate solution (1380 mL) was then added. When the color of iodine mostly disappeared, ethyl acetate (600 mL) was added, the mixture was stirred, and the two layers were separated. The organic layer was washed with water (150 mL) and a saturated saline (150 mL), dried with anhydrous sodium sulfate, and concentrated. The resulting residue was purified by silica gel column chromatography (hexane: ethyl acetate=1:1→5:6) to obtain titled compounds having the following physical property values (low polar compound 8.0 g; high polar compound 20.8 g).

High Polar Compound (Compound 5a)
  TLC: Rf 0.45 (ethyl acetate:hexane=1:1);
  NMR (CDCl$_3$): δ 4.65-4.5 (m, 2H), 4.25-3.6 (m, 5H), 3.55-3.45 (m, 1H), 2.7-2.2 (m, 3H), 2.2-1.5 (m, 16H), 0.95 (s, 9H), 0.12 and 0.11 (each are s, 3H).

Low Polar Compound (Compound 5b)
  TLC: Rf 0.50 (ethyl acetate:hexane=1:1);
  NMR (CDCl$_3$): δ 4.65-4.55 (m, 1H), 4.4-3.6 (m, 6H), 3.55-3.45 (m, 1H), 2.7-2.25 (m, 3H), 2.1-1.5 (m, 16H), 0.93 (s, 9H), 0.12 and 0.10 (each are s, 3H).

Example 6

(6R)-6-{2-[(1R,2S,3R,5R)-2-({[dimethyl(2-methyl-2-propanyl)silyl]oxy}methyl)-5-hydroxy-3-(tetrahydro-2H-pyran-2-yloxy)cyclopentyl]ethyl}tetrahydro-2H-pyran-2-one (compound 6)

To an anhydrous benzene (195 mL) solution of the compound 5a (41.8 g) were added tri-n-butyltin hydride (18.5 mL) and azobis(isobutyronitrile) (198 mg), and the mixture was heated to reflux for 3 hours. After allowing to cool, the reaction mixture was concentrated. The resulting residue was purified by silica gel column chromatography (hexane:ethyl acetate=4:1→1:1→2:3) to obtain a titled compound (29.9 g) having the following physical property values.
  TLC: Rf 0.50 (ethyl acetate:hexane=2:1);
  NMR (CDCl$_3$): δ 4.65-4.5 (m, 1H), 4.3-3.8 (m, 4H), 3.7-3.4 (m, 3H), 2.65-2.35 (m, 2H), 2.0-1.4 (m, 17H), 0.90 (s, 9H), 0.10 and 0.09 (each are s, 3H).

Example 7

Methyl (5R)-7-[(1R,2S,3R,5R)-2-({[dimethyl(2-methyl-2-propanyl)silyl]oxy}methyl)-5-hydroxy-3-(tetrahydro-2H-pyran-2-yloxy)cyclopentyl]-5-hydroxyheptanoate (compound 7)

To an anhydrous methanol (306 mL) solution of the compound 6 (33.2 g) was added triethylamine (25.5 mL), and the mixture was heated to reflux for 5 hours. After allowing to cool, the reaction mixture was concentrated. The resulting residue was azeotroped with toluene (two times) to obtain a titled compound (38.0 g) having the following physical property values.
  TLC: Rf 0.62 (ethyl acetate: dichloromethane=2:1);
  NMR (CDCl$_3$) δ 4.65-4.5 (m, 1H), 4.3-4.1 (m, 1H), 4.0-3.8 (m, 3H), 3.7-3.4 (m, 4H), 3.67 (s, 3H), 2.35 (t, J=7 Hz, 2H), 2.0-1.4 (m, 18H), 0.90 (s, 9H), 0.09 and 0.08 (each are s, 3H).

Example 8

Methyl (5R)-7-[(1R,2S,3R,5R)-2-({[dimethyl(2-methyl-2-propanyl)silyl]oxy}methyl)-5-[(methylsulfonyl)oxy]-3-(tetrahydro-2H-pyran-2-yloxy)cyclopentyl]-5-[(methylsulfonyl)oxy]heptanoate (compound 8)

An anhydrous dichloromethane (323 mL) solution of the compound 7 (38.0 g) and triethylamine (44 mL) was cooled to around −60° C. in a dry ice-methanol bath, and mesyl chloride (15 mL) was added dropwise over about 20 minutes. The bath was changed to an ice bath, the mixture was then stirred for 2 hours, and the reaction mixture was then added to cold water (600 mL), and extracted with a mixed solution of hexane (600 mL) and ethyl acetate (600 mL). The organic layer was washed with 1 M hydrochloric acid (290 mL) and a saturated saline (300 mL×3 times), dried with anhydrous sodium sulfate, and then concentrated to obtain a titled compound (44.7 g) having the following physical property values.
  TLC: Rf 0.82 (ethyl acetate: dichloromethane=2:1).

Example 9

Methyl 4-[(2S,4aR,5S,6R,7aS)-5-({[dimethyl(2-methyl-2-propanyl)silyl]oxy}methyl)-6-(tetrahydro-2H-pyran-2-yloxy)octahydrocyclopenta[b]thiopyran-2-yl]butanoate (compound 9)

A 70% sodium hydrosulfide n-hydrate (14.9 g) was added to methanol (123 mL), and the mixture was stirred at room temperature for 15 minutes, so that the sodium hydrosulfide n-hydrate was mostly dissolved. Thereto were added sodium hydrogen carbonate (15.9 g) and a methanol (200 mL) solution of the compound 8 (44.7 g), and the mixture was stirred at room temperature for 20 minutes, and then at 50° C. for 10 hours, and further stirred at room temperature for 4 hours. Thereafter, the mixture was raised to 60° C., stirred for 4 hours, and then cooled to room temperature. The reaction mixture was added to cold water (1200 mL), and extracted with a mixed solution of hexane (600 mL) and ethyl acetate (600 mL). The organic layer was washed with water (300 mL) and a saturated saline (300 mL), dried with anhydrous sodium sulfate, and concentrated. The resulting residue was purified by silica gel column chromatography (hexane:ethyl acetate=20:1) to obtain a titled compound (13.7 g) having the following physical property values.
  TLC: Rf 0.60 (ethyl acetate:hexane=1:4);
  NMR (CDCl$_3$): δ 4.65-4.6 (m, 1H), 4.0-3.8 (m, 2H), 3.68 (s, 3H), 3.65-3.4 (m, 3H), 3.1-2.9 (m, 1H), 2.85-2.7 (m, 1H), 2.4-2.2 (m, 3H), 2.1-1.4 (m, 16H), 0.87 (s, 9H), 0.04 (s, 6H).

Example 10

Methyl 4-[(2S,4aR,5S,6R,7aS)-5-(hydroxymethyl)-6-(tetrahydro-2H-pyran-2-yloxy)octahydrocyclopenta[b]thiopyran-2-yl]butanoate (compound 10)

To a tetrahydrofuran (74 mL) solution of the compound 9 (7.3 g) was added a 1 M tetrabutylammonium fluoride/tetrahydrofuran solution (27 mL), and the mixture was stirred for 3 hours. The reaction liquid was diluted with ethyl acetate (380 mL), washed with water (740 mL) and a saturated saline (380 mL). Further the aqueous layer was extracted with ethyl acetate (100 mL). The organic layers were combined, dried with anhydrous sodium sulfate, and concentrated. The resulting residue was purified by silica gel column chromatography (hexane:ethyl acetate=2:1). The resulting compound was purified again by silica gel column chromatography (dichloromethane:ethyl acetate=4:1→ethyl acetate) to obtain a titled compound (3.24 g) having the following physical property values.
  TLC: Rf 0.28 (ethyl acetate:hexane=1:1);
  NMR (CDCl$_3$): δ 1.23-2.19 (m, 17H), 2.24-2.40 (m, 3H), 2.69-2.82 (m, 1H), 2.92-3.02 (m, 1H), 3.44-3.73 (m, 6H), 3.82-4.07 (m, 2H), 4.55-4.74 (m, 1H).

Example 11

Methyl 4-[(2S,4aR,5R,6R,7aS)-5-formyl-6-(tetrahydro-2H-pyran-2-yloxy)octahydrocyclopenta[b]thiopyran-2-yl]butanoate (compound 11)

The compound 10 (200 mg) was dissolved in ethyl acetate (1.7 mL) and dimethyl sulfoxide (0.84 mL), diisopropylethylamine (0.39 mL) was added, and the mixture was cooled in an ice bath. Sulfur trioxide-pyridine (256 mg) was added, and the mixture was stirred for 10 minutes, then poured into water, and extracted with ethyl acetate. The organic layer was washed with water and a saturated saline, dried with anhydrous magnesium sulfate, and then concentrated to obtain a titled compound (200 mg) having the following physical property values.

TLC: Rf 0.51 (ethyl acetate:hexane=1:1).

Example 12

Methyl 4-[(2S,4aR,5R,6R,7aS)-5-[(1E)-3-oxo-4-phenoxy-1-buten-1-yl]-6-(tetrahydro-2H-pyran-2-yloxy)octahydrocyclopenta[b]thiopyran-2-yl]butanoate (compound 12)

To an anhydrous tetrahydrofuran (2.7 mL) solution of dimethyl (2-oxo-3-phenoxypropyl)phosphonate (194 mg) was added sodium hydride (24.8 mg) in an ice bath, and the mixture was stirred at room temperature for 1.5 hours. Thereto was added dropwise an anhydrous tetrahydrofuran (2 mL) solution of the compound 11 (200 mg), and the mixture was reacted at room temperature for 4.5 hours. Acetic acid was added in a small amount, and the reaction liquid was then diluted with ethyl acetate. This solution was washed with water and a saturated saline, dried with anhydrous magnesium sulfate, and then concentrated to obtain a titled compound (250 mg) having the following physical property values.

TLC: Rf 0.61 (ethyl acetate:hexane=1:1).

Example 13

Methyl 4-[(2S,4aR,5R,6R,7aS)-5-[(1E,3R)-3-hydroxy-4-phenoxy-1-buten-1-yl]-6-(tetrahydro-2H-pyran-2-yloxy)octahydrocyclopenta[b]thiopyran-2-yl]butanoate (compound 13)

The compound 12 (250 mg) and (R)-2-methyl-CBS-oxazaborolidine (1M toluene solution; 0.135 mL) were dissolved in anhydrous tetrahydrofuran (1 mL), and a 1M borane-tetrahydrofuran complex (0.323 mL) was added at room temperature. The mixture was stirred for 10 minutes, methanol was then added, and the mixture was stirred for several minutes. This reaction liquid was diluted with ethyl acetate. This solution was washed with 1 M hydrochloric acid, water and a saturated saline, dried with anhydrous magnesium sulfate, and then concentrated to obtain a titled compound (220 mg) having the following physical property values.

TLC: Rf 0.47 (ethyl acetate:hexane=1:1).

Example 14

Methyl 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoate (compound 14)

[Chemical formula 29]

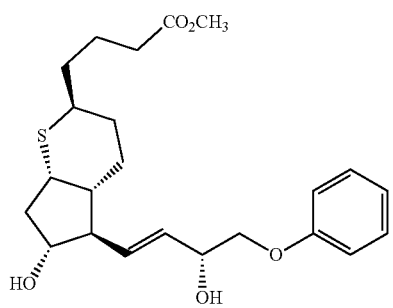

The compound 13 (220 mg) was dissolved in methanol (1.1 mL), a p-toluenesulfonic acid monohydrate (20 mg) was added at room temperature, and the mixture was stirred for 2 hours. The residue obtained by concentration of the reaction liquid under reduced pressure was purified by silica gel column chromatography (hexane:ethyl acetate=2:1→1:1→ethyl acetate) to obtain a titled compound (82 mg) having the following physical property values.

TLC: Rf 0.62 (ethyl acetate);

NMR (CDCl$_3$): δ 1.35-1.96 (m, 11H), 2.09-2.17 (m, 1H), 2.28-2.47 (m, 3H), 2.65-2.79 (m, 1H), 3.27-3.36 (m, 1H), 3.67 (s, 3H), 3.82-3.94 (m, 1H), 3.94-4.19 (m, 3H), 4.48-4.60 (m, 1H), 5.66 (dd, J=15.37, 5.67 Hz, 1H), 5.78 (dd, J=15.37, 8.42 Hz, 1H), 6.85-7.04 (m, 3H), 7.20-7.38 (m, 2H).

Example 14 (1) to Example 14 (3)

Using the compound 5a, or using the compound 5b in place thereof in Example 6, and using dimethyl [2-oxo-3-(phenyloxy)propyl]phosphonate, or using dimethyl (2-oxo-4-phenylbutyl)phosphonate in place thereof in Example 12, the same operations as those of Example 6→Example 7→Example 8→Example 9→Example 10→Example 11→Example 12→Example 13→Example 14 were performed to obtain the following compounds.

Example 14 (1)

Methyl 4-{(2R,4aR,5R,6R,7aS)-6-hydroxy-5-[(1E,3R)-3-hydroxy-5-phenyl-1-penten-1-yl]octahydrocyclopenta[b]thiopyran-2-yl}butanoate (compound 14 (1))

TLC: Rf 0.20 (hexane:ethyl acetate=1:1);

NMR (CDCl$_3$): δ 1.39-1.99 (m, 13H), 2.25-2.50 (m, 4H), 2.60-2.79 (m, 3H), 2.85-3.01 (m, 1H), 3.33-3.44 (m, 1H), 3.66 (s, 3H), 3.93-4.05 (m, 1H), 4.07-4.18 (m, 1H), 5.51 (dd, J=15.37, 8.42 Hz, 1H), 5.63 (dd, J=15.37, 6.40 Hz, 1H), 7.11-7.33 (m, 5H).

Example 14 (2)

Methyl 4-{(2S,4aR,5R,6R,7aS)-6-hydroxy-5-[(1E,3S)-3-hydroxy-5-phenyl-1-penten-1-yl]octahydrocyclopenta[b]thiopyran-2-yl}butanoate (compound 14 (2))

TLC: Rf 0.19 (hexane:ethyl acetate=1:1);
NMR (CDCl$_3$) δ 1.33-2.10 (m, 14H), 2.27-2.47 (m, 3H), 2.59-2.78 (m, 4H), 3.22-3.38 (m, 1H), 3.67 (s, 3H), 3.88-4.01 (m, 1H), 4.05-4.19 (m, 1H), 5.46-5.70 (m, 2H), 7.08-7.34 (m, 5H).

Example 14 (3)

Methyl 4-{(2R,4aR,5R,6R,7aS)-6-hydroxy-5-[(1E,3R)-3-hydroxy-4-phenoxy-1-buten-1-yl]octahydrocyclopenta[b]thiopyran-2-yl}butanoate (compound 14 (3))

TLC: Rf 0.61 (ethyl acetate);
NMR (CDCl$_3$): δ 1.37-1.94 (m, 11H), 2.23-2.50 (m, 4H), 2.62-2.76 (m, 1H), 2.90-3.04 (m, 1H), 3.36-3.44 (m, 1H), 3.67 (s, 3H), 3.82-3.94 (m, 1H), 3.95-4.07 (m, 2H), 4.48-4.60 (m, 1H), 5.61-5.82 (m, 2H), 6.87-7.01 (m, 3H), 7.22-7.34 (m, 2H).

Example 15

4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoic acid (compound 15)

[Chemical formula 30]

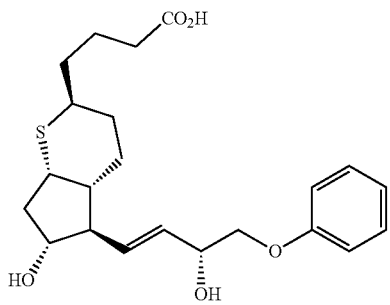

The compound 14 (6.9 mg) was dissolved in methanol (0.4 mL), a 2M aqueous sodium hydroxide solution (0.1 mL) was added at room temperature, and the mixture was stirred overnight. Dilute hydrochloric acid was added to the reaction liquid, and the mixture was then extracted with ethyl acetate two times. The organic layers were combined, washed with a saturated saline, and dried with anhydrous magnesium sulfate. The residue obtained by concentration under reduced pressure was purified by silica gel column chromatography (dichloromethane: methanol=100:1→10:1) to obtain a titled compound (4.8 mg) having the following physical property values.

TLC: Rf 0.41 (chloroform:methanol=9:1);
NMR (CDCl$_3$): δ 1.36-2.12 (m, 12H), 2.31-2.46 (m, 3H), 2.65-2.79 (m, 2H), 3.27-3.37 (m, 1H), 3.84-3.95 (m, 1H), 3.96-4.06 (m, 2H), 4.49-4.59 (m, 1H), 5.67 (dd, J=15.92, 5.67 Hz, 1H), 5.79 (dd, J=15.92, 7.87 Hz, 1H), 6.88-7.03 (m, 3H), 7.23-7.36 (m, 2H).

Example 15 (1) to Example 15 (20)

Using the compounds 14(1) to (3) or a corresponding ester in place of the compound 14, the same operations as those of Example 15 were performed to obtain the following compounds.

Example 15 (1)

4-{(2R,4aR,5R,6R,7aS)-6-hydroxy-5-[(1E,3S)-3-hydroxy-5-phenyl-1-penten-1-yl]octahydrocyclopenta[b]thiopyran-2-yl}butanoic acid (compound 15 (1))

TLC: Rf 0.25 (chloroform:methanol=9:1);
NMR (CDCl$_3$): δ 1.42-2.01 (m, 13H), 2.27-2.54 (m, 4H), 2.62-2.81 (m, 3H), 2.87-3.03 (m, 1H), 3.34-3.43 (m, 1H), 3.94-4.05 (m, 1H), 4.06-4.19 (m, 1H), 5.52 (dd, J=15.37, 8.42 Hz, 1H), 5.64 (dd, J=15.37, 6.40 Hz, 1H), 7.08-7.38 (m, 5H).

Example 15 (2)

4-{(2S,4aR,5R,6R,7aS)-6-hydroxy-5-[(1E,3S)-3-hydroxy-5-phenyl-1-penten-1-yl]octahydrocyclopenta[b]thiopyran-2-yl}butanoic acid (compound 15 (2))

TLC: Rf 0.25 (chloroform:methanol=9:1);
NMR (CDCl$_3$): δ 1.28-2.14 (m, 14H), 2.31-2.48 (m, 3H), 2.62-2.81 (m, 4H), 3.25-3.38 (m, 1H), 3.91-4.03 (m, 1H), 4.07-4.19 (m, 1H), 5.47-5.72 (m, 2H), 7.12-7.37 (m, 5H).

Example 15 (3)

4-{(2R,4aR,5R,6R,7aS)-6-hydroxy-5-[(1E,3R)-3-hydroxy-4-phenoxy-1-buten-1-yl]octahydrocyclopenta[b]thiopyran-2-yl}butanoic acid (compound 15 (3))

TLC: Rf 0.34 (ethyl acetate);
NMR (CDCl$_3$): δ 1.40-1.66 (m, 7H), 1.67-1.94 (m, 6H), 2.29-2.49 (m, 3H), 2.63-2.77 (m, 1H), 2.90-3.05 (m, 1H), 3.35-3.44 (m, 1H), 3.85-3.94 (m, 1H), 3.95-4.07 (m, 2H), 4.49-4.59 (m, 1H), 5.62-5.71 (m, 1H), 5.71-5.80 (m, 1H), 6.86-7.01 (m, 3H), 7.22-7.34 (m, 2H).

Example 15 (4)

4-{(2S,4aR,5R,6R,7aS)-5-[(1E,3R)-4-(4-fluorophenoxy)-3-hydroxy-1-buten-1-yl]-6-hydroxyoctahydrocyclopenta[b]thiopyran-2-yl}butanoic acid (compound 15 (4))

TLC: Rf 0.37 (dichloromethane: methanol=10:1);
NMR (CDCl$_3$): δ 1.18-1.93 (m, 11H), 1.95-2.13 (m, 1H), 2.24-2.54 (m, 3H), 2.62-2.81 (m, 2H), 3.19-3.44 (m, 1H), 3.78-3.91 (m, 1H), 3.91-4.04 (m, 2H), 4.45-4.58 (m, 1H), 5.58-5.70 (m, 1H), 5.70-5.87 (m, 1H), 6.76-6.91 (m, 2H), 6.91-7.04 (m, 2H).

Example 15 (5)

4-{(2S,4aR,5R,6R,7aS)-5-[(1E,3R)-4-(3-chlorophenoxy)-3-hydroxy-1-buten-1-yl]-6-hydroxyoctahydrocyclopenta[b]thiopyran-2-yl}butanoic acid (compound 15 (5))

TLC: Rf 0.37 (dichloromethane: methanol=10:1);
NMR (CDCl$_3$): δ 1.15-1.93 (m, 11H), 1.96-2.17 (m, 1H), 2.31-2.51 (m, 3H), 2.66-2.82 (m, 2H), 3.23-3.37 (m, 1H), 3.79-4.08 (m, 3H), 4.47-4.61 (m, 1H), 5.59-5.71 (m, 1H), 5.72-5.84 (m, 1H), 6.74-6.86 (m, 1H), 6.87-7.01 (m, 2H), 7.19 (t, J=8.05 Hz, 1H).

Example 15 (6)

4-{(2S,4aR,5R,6R,7aS)-6-hydroxy-5-[(1E,3R)-3-hydroxy-4-(3-methylphenoxy)-1-buten-1-yl]octahydrocyclopenta[b]thiopyran-2-yl}butanoic acid (compound 15 (6))

TLC: Rf 0.42 (dichloromethane: methanol=10:1);
NMR (CDCl$_3$): δ 1.12-2.16 (m, 10H), 2.28-2.49 (m, 6H), 2.64-2.82 (m, 2H), 3.25-3.36 (m, 1H), 3.86 (dd, J=9.33, 7.87 Hz, 3H), 3.92-4.05 (m, 2H), 4.43-4.61 (m, 1H), 5.52-5.72 (m, 1H), 5.72-5.86 (m, 1H), 6.61-6.85 (m, 3H), 7.17 (t, J=7.78 Hz, 1H).

Example 15 (7)

4-{(2S,4aR,5R,6R,7aS)-5-[(1E,3R)-4-(2-fluorophenoxy)-3-hydroxy-1-buten-1-yl]-6-hydroxyoctahydrocyclopenta[b]thiopyran-2-yl}butanoic acid (compound 15 (7))

TLC: Rf 0.36 (dichloromethane: methanol=10:1);
NMR (CDCl$_3$): δ 1.13-1.93 (m, 11H), 1.96-2.14 (m, 1H), 2.27-2.49 (m, 3H), 2.60-2.81 (m, 2H), 3.31 (q, J=5.67 Hz, 1H), 3.80-4.18 (m, 3H), 4.43-4.66 (m, 1H), 5.58-5.72 (m, 1H), 5.72-5.95 (m, 1H), 6.75-7.20 (m, 4H).

Example 15 (8)

4-{(2S,4aR,5R,6R,7aS)-5-[(1E,3R)-4-(3-fluorophenoxy)-3-hydroxy-1-buten-1-yl]-6-hydroxyoctahydrocyclopenta[b]thiopyran-2-yl}butanoic acid (compound 15 (8))

TLC: Rf 0.36 (dichloromethane: methanol=10:1);
NMR (CDCl$_3$): δ 1.17-2.11 (m, 12H), 2.24-2.55 (m, 3H), 2.59-2.82 (m, 2H), 3.31 (q, J=5.61 Hz, 1H), 3.73-4.11 (m, 3H), 4.46-4.60 (m, 1H), 5.59-5.86 (m, 2H), 6.52-6.85 (m, 3H), 7.08-7.33 (m, 1H).

Example 15 (9)

4-[(2S,4aR,5R,6R,7aS)-6-hydroxy-5-{(1E,3R)-3-hydroxy-4-[3-(trifluoromethyl)phenoxy]-1-buten-1-yl}octahydrocyclopenta[b]thiopyran-2-yl]butanoic acid (compound 15 (9))

TLC: Rf 0.46 (dichloromethane: methanol=10:1);
NMR (CDCl$_3$): δ 1.04-2.18 (m, 12H), 2.23-2.51 (m, 3H), 2.59-2.81 (m, 2H), 3.24-3.41 (m, 1H), 3.86-4.14 (m, 3H), 4.41-4.72 (m, 1H), 5.56-5.73 (m, 1H), 5.74-5.92 (m, 1H), 6.99-7.19 (m, 2H), 7.20-7.32 (m, 1H), 7.40 (t, J=8.05 Hz, 1H).

Example 15 (10)

4-{(2S,4aR,5R,6R,7aS)-6-hydroxy-5-[(1E,3R)-3-hydroxy-4-(2-methoxyphenoxy)-1-buten-1-yl]octahydrocyclopenta[b]thiopyran-2-yl}butanoic acid (compound 15 (10))

TLC: Rf 0.46 (dichloromethane: methanol=10:1);
NMR (CDCl$_3$): δ 1.15-2.23 (m, 12H), 2.29-2.49 (m, 3H), 2.59-2.78 (m, 2H), 3.21-3.40 (m, 1H), 3.80-4.21 (m, 6H), 4.44-4.61 (m, 1H), 5.54-5.68 (m, 1H), 5.68-5.85 (m, 1H), 6.84-7.02 (m, 4H).

Example 15 (11)

4-{(2S,4aR,5R,6R,7aS)-6-hydroxy-5-[(1E,3R)-3-hydroxy-4-(3-methoxyphenoxy)-1-buten-1-yl]octahydrocyclopenta[b]thiopyran-2-yl}butanoic acid (compound 15 (11))

TLC: Rf 0.46 (dichloromethane: methanol=10:1);
NMR (CDCl$_3$): δ 1.03-2.16 (m, 12H), 2.24-2.49 (m, 3H), 2.59-2.92 (m, 2H), 3.30 (q, J=5.73 Hz, 1H), 3.79 (s, 3H), 3.83-3.91 (m, 1H), 3.93-4.09 (m, 2H), 4.44-4.66 (m, 1H), 5.54-5.93 (m, 2H), 6.29-6.59 (m, 3H), 7.18 (t, J=8.14 Hz, 1H).

Example 15 (12)

4-{(2S,4aR,5R,6R,7aS)-6-hydroxy-5-[(1E,3R)-3-hydroxy-4-(4-methoxyphenoxy)-1-buten-1-yl]octahydrocyclopenta[b]thiopyran-2-yl}butanoic acid (compound 15 (12))

TLC: Rf 0.36 (dichloromethane: methanol=9:1);
NMR (CDCl$_3$): δ 1.10-1.94 (m, 11H), 1.95-2.12 (m, 1H), 2.28-2.53 (m, 3H), 2.62-2.81 (m, 2H), 3.24-3.36 (m, 1H), 3.77 (s, 3H), 3.78-3.86 (m, 1H), 3.89-4.15 (m, 2H), 4.37-4.61 (m, 1H), 5.46-5.70 (m, 1H), 5.70-5.93 (m, 1H), 6.57-6.96 (m, 4H).

Example 15 (13)

4-{(2S,4aR,5R,6R,7aS)-6-hydroxy-5-[(1E,3R)-3-hydroxy-4-(2-methylphenoxy)-1-buten-1-yl]octahydrocyclopenta[b]thiopyran-2-yl}butanoic acid (compound 15 (13))

TLC: Rf 0.32 (dichloromethane: methanol=9:1);
NMR (CDCl$_3$): δ 1.16-2.16 (m, 12H), 2.24 (s, 3H), 2.31-2.51 (m, 3H), 2.60-2.83 (m, 2H), 3.32 (q, J=5.55 Hz, 1H), 3.85-3.95 (m, 1H), 3.97-4.10 (m, 2H), 4.49-4.63 (m, 1H), 5.60-5.92 (m, 2H), 6.76-6.99 (m, 2H), 7.10-7.21 (m, 2H).

Example 15 (14)

4-{(2S,4aR,5R,6R,7aS)-6-hydroxy-5-[(1E,3R)-3-hydroxy-4-(4-methylphenoxy)-1-buten-1-yl]octahydrocyclopenta[b]thiopyran-2-yl}butanoic acid (compound 15 (14))

TLC: Rf 0.34 (dichloromethane: methanol=9:1);
NMR (CDCl$_3$): δ 1.29-1.91 (m, 11H), 1.94-2.11 (m, 1H), 2.29 (s, 3H), 2.32-2.47 (m, 3H), 2.62-2.84 (m, 2H), 3.23-3.35 (m, 1H), 3.64-3.89 (m, 1H), 3.90-4.11 (m, 2H), 4.38-4.60 (m, 1H), 5.53-5.70 (m, 1H), 5.71-5.86 (m, 1H), 6.80 (d, J=8.05 Hz, 2H), 7.07 (d, J=8.05 Hz, 2H).

Example 15 (15)

4-{(2S,4aR,5R,6R,7aS)-5-[(1E,3R)-4-(4-chlorophenoxy)-3-hydroxy-1-buten-1-yl]-6-hydroxyoctahydrocyclopenta[b]thiopyran-2-yl}butanoic acid (compound 15 (15))

TLC: Rf 0.36 (dichloromethane: methanol=9:1);
NMR (CDCl$_3$): δ 1.04-2.14 (m, 12H), 2.29-2.56 (m, 3H), 2.61-2.78 (m, 2H), 3.19-3.44 (m, 1H), 3.75-3.91 (m, 1H), 3.91-4.11 (m, 2H), 4.42-4.60 (m, 1H), 5.57-5.70 (m, 1H), 5.72-5.89 (m, 1H), 6.81-6.88 (m, 2H), 7.14-7.27 (m, 2H).

Example 15 (16)

4-{(2S,4aR,5R,6R,7aS)-5-[(1E,3R)-4-(2-chlorophenoxy)-3-hydroxy-1-buten-1-yl]-6-hydroxyoctahydrocyclopenta[b]thiopyran-2-yl}butanoic acid (compound 15 (16))

TLC: Rf 0.48 (dichloromethane: methanol=9:1);
NMR (CDCl$_3$): δ 1.14-1.92 (m, 11H), 1.93-2.15 (m, 1H), 2.31-2.49 (m, 3H), 2.63-2.79 (m, 2H), 3.30 (q, J=5.61 Hz, 1H), 3.82-4.20 (m, 3H), 4.50-4.63 (m, 1H), 5.56-5.70 (m, 1H), 5.72-5.84 (m, 1H), 6.82-6.99 (m, 2H), 7.17-7.24 (m, 1H), 7.35 (dd, J=8.14, 1.19 Hz, 1H).

Example 15 (17)

4-[(2S,4aR,5R,6R,7aS)-6-hydroxy-5-{(1E,3R)-3-hydroxy-4-[2-(trifluoromethyl)phenoxy]-1-buten-1-yl}octahydrocyclopenta[b]thiopyran-2-yl]butanoic acid (compound 15 (17))

TLC: Rf 0.48 (dichloromethane: methanol=9:1);
NMR (CDCl$_3$): δ 1.18-1.94 (m, 11H), 1.94-2.17 (m, 1H), 2.30-2.47 (m, 3H), 2.64-2.83 (m, 2H), 3.24-3.37 (m, 1H), 3.85-4.16 (m, 3H), 4.48-4.59 (m, 1H), 5.54-5.72 (m, 1H), 5.73-5.88 (m, 1H), 6.88-7.09 (m, 2H), 7.48 (t, J=7.96 Hz, 1H), 7.56 (d, J=7.68 Hz, 1H).

Example 15 (18)

4-[(2S,4aR,5R,6R,7aS)-6-hydroxy-5-{(1E,3R)-3-hydroxy-4-[4-(trifluoromethyl)phenoxy]-1-buten-1-yl}octahydrocyclopenta[b]thiopyran-2-yl]butanoic acid (compound 15 (18))

TLC: Rf 0.48 (dichloromethane: methanol=9:1);
NMR (CDCl$_3$): δ 1.20-1.94 (m, 11H), 1.95-2.19 (m, 1H), 2.28-2.50 (m, 3H), 2.62-2.83 (m, 2H), 3.16-3.43 (m, 1H), 3.80-4.13 (m, 3H), 4.44-4.63 (m, 1H), 5.59-5.71 (m, 1H), 5.72-5.91 (m, 1H), 6.97 (d, J=8.60 Hz, 2H), 7.54 (d, J=8.60 Hz, 2H).

Example 15 (19)

4-{(2S,4aR,5R,6R,7aS)-6-hydroxy-5-[(1E,3R)-3-hydroxy-4-(phenylthio)-1-buten-1-yl]octahydrocyclopenta[b]thiopyran-2-yl}butanoic acid (compound 15 (19))

TLC: Rf 0.48 (dichloromethane: methanol=9:1);
NMR (CDCl$_3$): δ 1.13-1.94 (m, 11H), 1.93-2.13 (m, 1H), 2.27-2.48 (m, 3H), 2.57-2.80 (m, 2H), 2.90-3.07 (m, 1H), 3.08-3.23 (m, 1H), 3.27 (q, J=5.43 Hz, 1H), 3.85-3.99 (m, 1H), 4.10-4.27 (m, 1H), 5.31-5.74 (m, 2H), 7.02-7.51 (m, 5H).

Example 15 (20)

4-{(2S,4aR,5R,6R,7aS)-6-hydroxy-5-[(3R)-3-hydroxy-4-phenoxybutyl]octahydrocyclopenta[b]thiopyran-2-yl}butanoic acid (compound 15 (20))

TLC: Rf 0.48 (dichloromethane: methanol=9:1);
NMR (CDCl$_3$): δ 1.34-2.15 (m, 17H), 2.21-2.34 (m, 1H), 2.39 (t, J=6.95 Hz, 2H), 2.64-2.84 (m, 1H), 3.12-3.31 (m, 1H), 3.69-4.25 (m, 4H), 6.79-7.10 (m, 3H), 7.21-7.45 (m, 2H).

Example 16

2-propanyl 4-{(2S,4aR,5R,6R,7aS)-6-hydroxy-5-[(3R)-3-hydroxy-4-phenoxybutyl]octahydrocyclopenta[b]thiopyran-2-yl}butanoate (compound 16)

[Chemical formula 31]

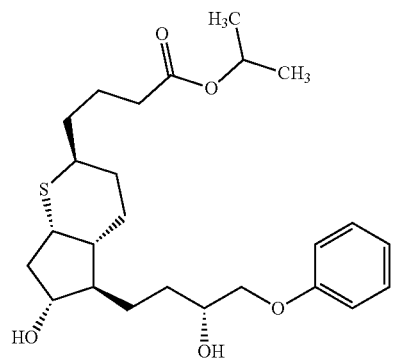

Under the argon atmosphere, cesium carbonate (68 mg) and isopropyl iodide (0.016 mL) were added to a dimethylformamide (0.4 mL) solution of the compound 15 (20) (42.8 mg), and the mixture was stirred at 50° C. for 90 minutes. This was cooled to room temperature, ethyl acetate was then added, and the mixture was washed with water two times, and then with a saturated saline once. The mixture was dried with anhydrous magnesium sulfate, and then concentrated. The resulting residue was purified by silica gel column chromatography (hexane:ethyl acetate=7:3→1:1) to obtain a titled compound (34 mg) having the following physical property values.

TLC: Rf 0.57 (hexane:ethyl acetate=1:2)
NMR (CDCl$_3$): δ 1.23 (d, J=6.22 Hz, 6H), 1.36-2.11 (m, 15H), 2.14-2.53 (m, 5H), 2.65-2.81 (m, 1H), 3.19 (q, J=6.10 Hz, 1H), 3.65-4.34 (m, 4H), 5.00 (tt, J=6.27 Hz, 1H), 6.65-7.06 (m, 3H), 7.21-7.40 (m, 2H).

Example 16 (1) to Example 16 (9)

Using a corresponding carboxylic acid in place of the compound 15 (20), the same operations as those of Example 16 were performed to obtain the following compounds.

Example 16 (1)

2-Propanyl 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl}butanoate (compound 16 (1))

TLC: Rf 0.41 (hexane:ethyl acetate=1:2);
NMR (CDCl$_3$): δ 1.23 (d, J=6.22 Hz, 6H), 1.33-1.92 (m, 9H), 1.95-2.21 (m, 2H), 2.24-2.33 (m, 2H), 2.33-2.43 (m, 1H), 2.45 (d, J=3.48 Hz, 1H), 2.63-2.84 (m, 2H), 3.26-3.38 (m, 1H), 3.82-3.95 (m, 1H), 3.95-4.07 (m, 2H), 4.46-4.65 (m, 1H), 4.93-5.07 (m, 1H), 5.57-5.71 (m, 1H), 5.71-5.85 (m, 1H), 6.82-7.03 (m, 3H), 7.21-7.34 (m, 2H).

Example 16 (2)

2-Propanyl 4-{(2S,4aR,5R,6R,7aS)-5-[(1E,3R)-4-(3-chlorophenoxy)-3-hydroxy-1-buten-1-yl]-6-hydroxyoctahydrocyclopenta[b]thiopyran-2-yl}butanoate (compound 16 (2))

TLC: Rf 0.40 (hexane:ethyl acetate=1:2);
NMR (CDCl$_3$): δ 1.22 (d, J=6.22 Hz, 6H), 1.35-1.89 (m, 9H), 1.90-2.14 (m, 1H), 2.19-2.58 (m, 4H), 2.61-2.84 (m, 3H), 3.18-3.34 (m, 1H), 3.83-3.92 (m, 1H), 3.92-4.05 (m, 2H), 4.43-4.64 (m, 1H), 4.91-5.09 (m, J=6.27, 6.27, 6.27, 6.27 Hz, 1H), 5.59-5.69 (m, 1H), 5.70-5.82 (m, 1H), 6.80 (ddd, J=8.37, 2.42, 0.91 Hz, 1H), 6.88-7.02 (m, 2H), 7.19 (t, J=8.05 Hz, 1H).

Example 16 (3)

2-Propanyl 4-{(2S,4aR,5R,6R,7aS)-6-hydroxy-5-[(1E,3R)-3-hydroxy-4-(3-methylphenoxy)-1-buten-1-yl]octahydrocyclopenta[b]thiopyran-2-yl}butanoate (compound 16 (3))

TLC: Rf 0.43 (hexane:ethyl acetate=1:2);
NMR (CDCl$_3$): δ 1.23 (d, J=6.22 Hz, 6H), 1.34-2.11 (m, 10H), 2.20-2.49 (m, 7H), 2.53-2.81 (m, 3H), 3.22-3.41 (m, 1H), 3.77-3.94 (m, 1H), 3.91-4.08 (m, 2H), 4.31-4.61 (m, 1H), 4.82-5.09 (m, 1H), 5.49-5.70 (m, 1H), 5.71-5.95 (m, 1H), 6.49-6.87 (m, 3H), 7.16 (t, J=7.78 Hz, 1H).

Example 16 (4)

2-Propanyl 4-{(2S,4aR,5R,6R,7aS)-5-[(1E,3R)-4-(3-fluorophenoxy)-3-hydroxy-1-buten-1-yl]-6-hydroxyoctahydrocyclopenta[b]thiopyran-2-yl}butanoate (compound 16 (4))

TLC: Rf 0.33 (hexane:ethyl acetate=1:2);
NMR (CDCl$_3$): δ 1.23 (d, J=6.22 Hz, 6H), 1.33-1.95 (m, 9H), 1.96-2.08 (m, 1H), 2.21-2.46 (m, 4H), 2.49-2.57 (m, 1H), 2.65-2.85 (m, 2H), 3.23-3.42 (m, 1H), 3.78-3.93 (m, 1H), 3.93-4.08 (m, 2H), 4.42-4.67 (m, 1H), 4.85-5.15 (m, 1H), 5.47-5.71 (m, 1H), 5.73-6.03 (m, 1H), 6.49-6.95 (m, 3H), 7.03-7.27 (m, 1H).

Example 16 (5)

2-Propanyl 4-{(2S,4aR,5R,6R,7aS)-5-[(1E,3R)-4-(4-fluorophenoxy)-3-hydroxy-1-buten-1-yl]-6-hydroxyoctahydrocyclopenta[b]thiopyran-2-yl}butanoate (compound 16 (5))

TLC: Rf 0.41 (hexane:ethyl acetate=1:2);
NMR (CDCl$_3$): δ 1.23 (d, J=6.22 Hz, 6H), 1.34-1.94 (m, 9H), 1.97-2.11 (m, 1H), 2.20-2.47 (m, 4H), 2.55-2.86 (m, 3H), 3.32 (q, J=5.85 Hz, 1H), 3.74-4.05 (m, 3H), 4.47-4.57 (m, 1H), 4.90-5.15 (m, 1H), 5.52-5.71 (m, 1H), 5.71-5.88 (m, 1H), 6.81-6.91 (m, 2H), 6.93-7.06 (m, 2H).

Example 16 (6)

2-Propanyl 4-{(2S,4aR,5R,6R,7aS)-6-hydroxy-5-[(1E,3R)-3-hydroxy-4-(3-methoxyphenoxy)-1-buten-1-yl]octahydrocyclopenta[b]thiopyran-2-yl}butanoate (compound 16 (6))

TLC: Rf 0.32 (hexane:ethyl acetate=1:1);
NMR (CDCl$_3$): δ 1.23 (d, J=6.22 Hz, 6H), 1.35-1.91 (m, 9H), 1.93-2.09 (m, 1H), 2.18-2.55 (m, 4H), 2.57-2.82 (m, 3H), 3.22-3.36 (m, 1H), 3.78 (s, 3H), 3.82-3.90 (m, 1H), 3.92-4.07 (m, 2H), 4.45-4.55 (m, 1H), 4.88-5.08 (m, 1H), 5.59-5.69 (m, 1H), 5.70-5.82 (m, 1H), 6.29-6.58 (m, 3H), 7.17 (t, J=8.14 Hz, 1H).

Example 16 (7)

2-Propanyl 4-{(2S,4aR,5R,6R,7aS)-6-hydroxy-5-[(1E,3R)-3-hydroxy-4-(2-methoxyphenoxy)-1-buten-1-yl]octahydrocyclopenta[b]thiopyran-2-yl}butanoate (compound 16 (7))

TLC: Rf 0.26 (hexane:ethyl acetate=1:1);
NMR (CDCl$_3$) 1.23 (d, J=6.40 Hz, 6H), 1.34-1.91 (m, 9H), 1.93-2.09 (m, 1H), 2.21-2.51 (m, 4H), 2.62-2.77 (m, 2H), 3.16-3.42 (m, 2H), 3.90 (dd, 5H), 4.06 (dd, J=9.88, 3.11 Hz, 1H), 4.44-4.58 (m, 1H), 4.92-5.08 (m, 1H), 5.49-5.67 (m, 1H), 5.68-5.88 (m, 1H), 6.79-7.11 (m, 4H).

Example 16 (8)

2-Propanyl 4-{(2S,4aR,5R,6R,7aS)-6-hydroxy-5-[(1E,3R)-3-hydroxy-4-(phenylthio)-1-buten-1-yl]octahydrocyclopenta[b]thiopyran-2-yl}butanoate (compound 16 (8))

TLC: Rf 0.46 (hexane:ethyl acetate=1:3);
NMR (CDCl$_3$): δ 1.23 (d, J=6.40 Hz, 6H), 1.32-1.89 (m, 9H), 1.93-2.09 (m, 1H), 2.17-2.45 (m, 3H), 2.49-2.79 (m, 3H), 2.79-3.05 (m, 2H), 3.09-3.18 (m, 1H), 3.22-3.35 (m, 1H), 3.83-4.04 (m, 1H), 4.11-4.25 (m, 1H), 4.87-5.15 (m, 1H), 5.49-5.68 (m, 2H), 7.16-7.26 (m, 1H), 7.28-7.33 (m, 2H), 7.35-7.48 (m, 2H).

Example 16 (9)

2-Propanyl 4-[(2S,4aR,5R,6R,7aS)-6-hydroxy-5-{(1E,3R)-3-hydroxy-4-[3-(trifluoromethyl)phenoxy]-1-buten-1-yl}octahydrocyclopenta[b]thiopyran-2-yl]butanoate (compound 16 (9))

TLC: Rf 0.54 (hexane:ethyl acetate=1:2);
NMR (CDCl$_3$): δ 1.23 (d, J=6.22 Hz, 6H), 1.38-1.91 (m, 9H), 1.95-2.11 (m, 1H), 2.20-2.48 (m, 4H), 2.50-2.59 (m, 1H), 2.62-2.83 (m, 2H), 3.25-3.39 (m, 1H), 3.85-4.14 (m, 3H), 4.48-4.64 (m, 1H), 4.91-5.08 (m, J=6.27, 6.27, 6.27, 6.27 Hz, 1H), 5.61-5.72 (m, 1H), 5.74-5.87 (m, 1H), 6.97-7.17 (m, 2H), 7.18-7.29 (m, 1H), 7.39 (t, J=8.05 Hz, 1H).

Pharmacological Experimental Example (1) In Vitro Test
(1-1) Measurement of Agonist Activity on Various Mouse Prostanoid Receptors
Using CHO cells (FP-CHO, EP2-CHO, EP4-CHO and IP-CHO, respectively) in which various mouse prostanoid receptors were forcibly expressed, respectively, agonist activity of test compounds on various prostanoid receptors was studied employing an intracellular calcium concentration regarding FP, and an intracellular cyclic AMP (hereinafter, abbreviated as cAMP) production amount regarding IP, EP2 and EP4 as an index.

<Compound Treatment>

The test compound and a control substance (PGE2, PGF$_{2\alpha}$, and iroprost) were dissolved with dimethyl sulfoxide (DMSO) to prepare a 10 mmol/L solution. Regarding the prepared 10 mmol/L solution, upon use, the 10 mmol/L solution was thawed, stepwisely-diluted using DMSO, and diluted with a buffer solution for measurement or a buffer solution for measurement 2, which was subjected to an experiment.

<Cell Culturing>

Cells forcibly expressing various mouse prostanoid receptors were standing-cultured at 37° C. in the presence of 5% $CO_2$ using an α-MEM medium (Sigma) (for culturing FP-CHO, EP2-CHO and EP4-CHO) containing inactivated (56° C., 30 minutes) 9.8 vol % dialysed-FBS (Invitrogen) and penicillin-streptomycin-glutamine (GIBCO-BRL), or nucleic acid-containing α-MEM (Sigma) (for culturing IP-CHO) containing inactivated (56° C., 30 minutes) 9.8 vol % dialysed-FBS (Invitrogen) and penicillin-streptomycin-glutamine (Invitrogen). Subculturing was performed by the following method.

The medium was removed, and washed with a phosphate-buffered physiological saline not containing $Ca^{2+}$ and $Mg^{2+}$ once. A suitable amount of trypsin-EDTA (Invitrogen) was added, this was incubated at 37° C. for about 3 minutes, cells were peeled, and a medium having a volume which is 10-fold a volume of trypsin-EDTA was added to stop an enzymatic reaction. After cells were recovered (120 g) into a centrifuging tube, and centrifuged at room temperature for 3 minutes, the supernatant was removed. Cells were suspended in a suitable amount of a medium, and seeded in a culturing flask.

(1-2) Measurement of FP Agonist Activity (Measurement of Intracellular Calcium Concentration)

Regarding FP-CHO, by the same method as that of subculturing, cells were peeled and suspended and, before two days from measurement, the suspension was seeded on a 96-well UV plate so that the cell number per well became $1.0 \times 10^4$, and standing-cultured at 37° C. in the presence of 5% $CO_2$. On the measurement day, after the medium was removed from each well of the 96-well UV plate, each well was washed with a phosphate-buffered physiological saline not containing $Ca^{2+}$ and $Mg^{2+}$ once. To each well was added 100 μL of a medium containing 5 μmol/L fura 2-AM (DOJINDO), 2.5 mmol/L Probenecid (Sigma), 20 μmol/L indometacin (Sigma) and 10 mmol/L HEPES (Invitrogen), and this was incubated for about 60 minutes in a $CO_2$ incubator. After completion of the incubation, the medium was removed, and this was washed with a buffer solution for measurement (Hank's balanced salt solution) (Invitrogen) containing 0.1 w/v % bovine serum albumin, 2 μmmol/L indometacin, 2.5 mmol/L Probenecid and 20 mmol/L HEPES (Invitrogen) two times. To each well was added 120 μL of a buffer solution for measurement, and this was allowed to stand in a dark place at room temperature for 30 minutes, and stabilized, which was subjected to an experiment.

The 96-well UV plate was set in a fluorescent spectral photometer (FDSS-3000, Hamamatsu Photonics K.K.), and an intracellular calcium concentration was measured. A buffered solution for measurement (30 μL) containing an agonist at a variety of concentrations was added to perform a reaction. Measurement of an intracellular calcium concentration was performed by irradiating cells with excited light of 340 nm and 380 nm alternately, measuring a fluorescent intensity at 500 nm, and obtaining a fluorescent intensity ratio of 2-wavelength excitation.

(1-3) Measurement of EP2, EP4 and IP Agonist Activity (Measurement of cAMP Concentration)

On the measurement day, a medium was removed, and EP2-CHO, EP4-CHO and IP-CHO were washed with a phosphate-buffered physiological saline containing 2 mmol/L EDTA and not containing $Ca^{2+}$ and $Mg^{2+}$ once. A suitable amount of a phosphate-buffered physiological saline containing 2 mmol/L EDTA and not containing $Ca^{2+}$ and $Mg^{2+}$ was added, this was incubated at room temperature for about 5 minutes, cells were peeled, cells were recovered (550 g) into a centrifuging tube, and centrifuged at room temperature for 3 minutes, and the supernatant was removed. Cells were suspended in a suitable amount of a buffer solution for measurement 1 (MEM medium (Invitrogen) containing 1.0 w/v % bovine serum albumin (Sigma) and 2 μmol/L diclofenac (Sigma)), and centrifuged at room temperature for 3 minutes at 500 g, and the supernatant was removed. Cells were suspended in a buffer solution for measurement 2 (MEM medium (Invitrogen) containing 1.0 w/v % bovine serum albumin (Sigma), 2 μmol/L diclofenac (Sigma) and 1 mmol/L 3-isobutyl-1-methylxanthine), and each 25 μL of the suspension was dispensed into a 96-well 1/2 area plate so that the cell number per well became $5.0 \times 10^4$. A buffer solution for measurement 2 (25 μL) containing an agonist at a variety of concentrations was added to perform a reaction at room temperature for 30 minutes. Measurement of a cAMP concentration was performed using the cAMP HTRF HiRange kit (CIS bio International). According to the two step protocol of the kit manual, each 25 μL of cAMP-D2 and Cryptase diluted with a lysis buffer were added, and this was incubated at room temperature for 1 hour. After incubation for 1 hour, time resolution fluorescence at 620 nm and 665 nm when excited at 337 nm was measured using Analyst GT (Molecular Device), and a ratio (TRF ratio) was obtained, thereby, a cAMP concentration was calculated from a calibration line.

<Result>

Using measured values obtained from the above method, an EC50 value as an index of agonist activity of the present invention compound on mouse FP, mouse EP2, mouse EP4 and mouse IP receptors was calculated.

For example, results for the compound described in Example 15, and the compound of Example 12, as a comparative compound, described in Patent Literature 2 which is represented by the following structural formula:

[Chemical formula 32]

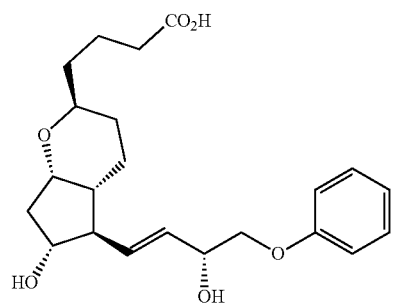

(hereinafter, abbreviated as Comparative Compound A in some cases) and 4-{(2S,4aR,5R,6R,7aS)-6-hydroxy-5-[(1E, 3S)-3-hydroxy-1-octen-1-yl]octahydrocyclopenta[b]thiopyran-2-yl}butanoic acid that is an optically active body (2S isomer) and carboxylic acid of the compound described in Example 1 (F) described in Patent Literature 1, which is represented by the following structural formula:

[Chemical formula 33]

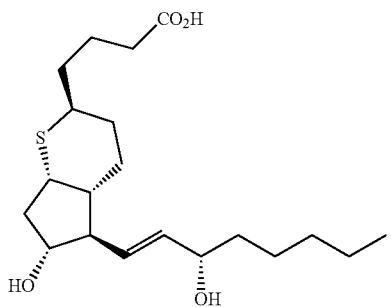

(hereinafter, abbreviated as Comparative Compound B in some cases) as comparative compounds are shown in Table 1.

TABLE 1

| | Agonist activity on various prostanoid receptors: $EC_{50}$ value (μmol/L) | | | |
|---|---|---|---|---|
| | FP | EP2 | EP4 | IP |
| Example 15 | 0.0034 | >100 | >100 | 6.1 |
| Comparative Compound A | 0.0011 | >100 | 6.1 | 0.71 |
| Comparative Compound B | 0.0089 | 0.022 | 0.38 | 0.89 |

From the above results, the Comparative Compound A has agonist activity not only on an FP receptor, but also on an IP receptor, and the Comparative Compound B has agonist activity on EP2, EP4 and IP receptors in addition to agonist activity on an FP receptor. In contrast, the present invention compound was found to have low agonist activity on EP2, EP4 and IP receptors and have selective agonist activity on an FP receptor.

(2) In Vivo Test

As can be easily understood by a person skilled in the art, in an in vivo test, since regarding all test compounds, carboxylic acid which is an active body bad corneal permeability, pharmacological action of the active body was assessed by ocular instillation administration of a compound which had been converted into an ester such as an ethyl ester, an isopropyl ester etc. In addition, in a group of the present invention compounds, by ocular instillation-administering the ester body in an experimental animal (rabbit, dog etc.) by which pharmacological action is confirmed below and, thereafter, measuring a drug concentration of carboxylic acid in an aqueous humor, it was confirmed that the ester is rapidly converted into corresponding carboxylic acid.

(2-1) Intraocular Pressure Lowering Action

To one eye of a male dog (TOYO Beagle) which had been sufficiently acclimated in advance was ocular-instilled 30 μL of the compound of Example 16 (1) which had been adjusted with a base (containing citrate buffer pH 6.5, 0.5% polysorbate 80, 1% propylene glycol, 0.01% benzalkonium chloride) to 0.003% (w/v), respectively. The other eye was not treated. As a positive control compound, latanoprost which is the known compound was used.

Thereafter, an ocular surface anesthetic (Benoxil eye drops 0.4%, Santen Pharmaceutical Co., Ltd.) was subjected to ocular instillation to locally anesthetize eyes, and an intraocular pressure of each test compound before ocular instillation and after 2, 4, 6, 8, and 24 hours from ocular instillation was measured. An intraocular pressure was measured using a pneumatic applanation flat tonometer (Model 30 Classic, REICHERT). An intraocular pressure lowering rate (%) was calculated by the following equation.

[Mathematic 1]

$$\text{Intraocular pressure lowering rate (\%)} = \frac{\left(\begin{array}{c}\text{intraocular pressure value}\\ \text{before ocular instillation} -\\ \text{intraocular pressure value}\\ \text{at each point}\end{array}\right)}{\text{intraocular pressure value before ocular instillation}} \times 100$$

Among measured values at each point, the result showing the maximum action is shown in Table 2. The intraocular pressure of a dog to which the compound of Example 16 (1) was ocular instillation-administered exhibited the stronger intraocular pressure lowering action as compared with latanoprost which is a positive control compound.

TABLE 2

| Compound | Administration dose (μg/mL) | Number of examples | Maximum of intraocular pressure lowering rate (%) |
|---|---|---|---|
| Example 16 (1) | 30 | 9 | 34.2 |
| Latanoprost | 50 | 10 | 25.4 |

(2-2) Assessment of Ocular Stimulating Property and Aqueous Humor Protein Concentration To one eye of a male rabbit (NewZealandWhite, 2.0 to 3.0 kg) was ocular-instilled 30 μL of the compound of Example 16 (1) which had been adjusted to 0.1% (w/v) with a base (containing citrate buffer pH 6.5, 0.5% polysorbate 80, 1% propylene glycol, 0.01% benzalkonium chloride), respectively. Thereafter, an aqueous humor in anterior chamber after 0, 1, 2, 4, 6 and 8 hours from ocular instillation was collected, and a protein concentration in the humor was measured. As comparative compounds, the aforementioned methyl ester of the compound of Example 12 described in Patent Literature 2 (i.e. compound of Example 10 described in Patent Literature 2) (hereinafter, abbreviated as Comparative Compound C in some cases) and the aforementioned methyl ester of the Comparative Compound B (i.e. optically active body (2S isomer) of the compound of Example 1 (F) described in Patent Literature 1) (hereinafter, abbreviated as Compound D in some cases) were used.

Observation of the ocular general state was performed after 0, 1, 2, 4, 6 and 8 hours from ocular instillation, and visual remark of cornea, iris, and conjunctiva was observed according to determination criteria of the Draize method. A total of points of the resulting assessment points of each item ($=A_1 \times B_1 \times 5 + A_2 \times 5 + (A_3 + B_3 + C_3) \times 2$) was assessed as a Draize score. Classification criteria of the Draize score was produced by referring to "Regarding Reference Material concerning Basic Idea of Biological Safety Test, Administrative Notice Medical Device Examination No. 36 dated Mar. 19, 2003, Pharmaceutical and Medical Devices Agency". Classification criteria was as follows: A Draize score of 0 or more and 5 or less was a non-stimulating substance, 5 or more and 15 or less was a slightly stimulating substance, 15 or more and 30 or less was a stimulating substance, 30 or more and 60 or less was an intermediate stimulating substance, 60 or more and 80 or less was an intermediate to strongly stimulating substance, and 80 or more and 110 or less was a strongly stimulating substance.

Regarding any test compound, a dose of 1000 µg/mL was administered and action of each active body was assessed.

Figure 2:
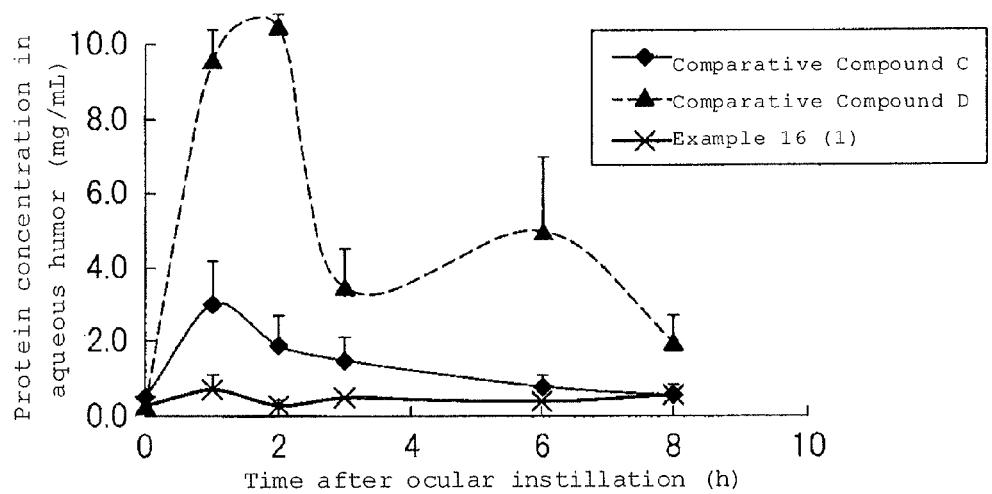
FIG. 2A graph expressing transition of a concentration of a protein in a humor after ocular instillation of the present invention compound and a comparative compound.

Results are shown in the following FIG. 1 and FIG. 2. The Comparative Compounds C and D were classified as a slightly stimulating substance from a maximum of the Draize score, based on its agonist activity on an IP receptor or IP, EP2 and EP4 agonist activity. Further, both the compounds were found to induce the side effect on eyes because they raise a protein concentration in an aqueous humor. To the contrary, it was seen that the compound of Example 16 (1) which is the present invention compound was a non-stimulating substance by the Draize score, and had no action of raising a protein concentration in an aqueous humor.

From the foregoing, since the present invention compound has low agonist activity on EP2, EP4 and IP receptors, and has selective agonist activity on an FP receptor, it was suggested that side effects on eyes such as ocular stimulating properties such as hyperemia and aqueous humor protein rise etc. based on EP2, EP4 and IP receptor agonist activity can be avoided.

(2-3) Intraocular Pressure Lowering Action in Monkey Under Consciousness

To a left eye of a male monkey (crab-eating monkey) under consciousness was ocular instillation-administered 30 µL of a solution obtained by adjusting a test substance using the same base as that described above and, to a right eye was ocular instillation-administered 30 µL of a solution of only a base as a control, respectively. An intraocular pressure after administration was measured with time from administration initiation to after 24 hours. Upon measurement of an intraocular pressure, a crab-eating monkey was fixed on a monkey chair, and the monkey was anesthetized by ocular instillation-administering an ocular surface anesthetic (Benoxil eye drops 0.4% Santen Pharmaceutical Co., Ltd.). After mounting of a blepharostat (Handaya Co., Ltd.), an intraocular pressure of both eyes was measured (5 to 8 examples per group) using a pneumatic applanation flat tonometer (Model 30 Classic, REICHERT). A difference in an intraocular pressure value between control eyes and eyes to which a test substance had been administered, was calculated as an intraocular pressure lowering rate using the following equation, and sustainability of intraocular eye lowering action was assessed using a maximum intraocular pressure lowering rate during measurement and an intraocular pressure lowering rate after 24 hours. The administration dose of the test substance was 10 µg/mL for the Comparative Compound C and 30 µg/mL for Example 16 (1).

[Mathematic 2]
$$\text{Intraocular pressure lowering rate } (\%) = \frac{\left(\begin{array}{c}\text{intraocular pressure value}\\\text{of control eye} -\\\text{intraocular pressure value of}\\\text{test substance-administered eye}\end{array}\right)}{\text{intraocular pressure value of control eye}} \times 100$$

The results are shown in the following Table 3. It was seen that, in the Comparative Compound C, a maximum intraocular pressure lowering rate was insufficient and, additionally, the lowering rate was reduced to less than 10% after 24 hours, and intraocular pressure lowering action cannot be sufficiently maintained. To the contrary, it was seen that all of the present invention compounds are compounds which have a high maximum intraocular pressure lowering rate, and can maintain an intraocular pressure lowering rate of about 20% or more even after 24 hours, and have strong and sustaining intraocular pressure lowering action.

TABLE 3

| Compound | Number of examples | Maximum intraocular pressure lowering rate (%) | Intraocular pressure lowering rate after 24 hours (%) |
|---|---|---|---|
| Comparative Compound C | 5 | 13.2 ± 3.2 | 7.0 ± 0.9 |
| Example 16 (1) | 8 | 25.3 ± 2.4 | 23.1 ± 2.7 |

From the foregoing, since the present invention compound has low agonist activity on EP2, EP4 and IP receptors, and has selective agonist activity on an FP receptor, it was suggested that not only the compound permanently has strong intraocular pressure lowering action, but also side effects on eyes such as ocular stimulating properties such as hyperemia and aqueous humor protein rise etc. based on EP2, EP4 and IP receptor agonist activity can be avoided.

PREPARATION EXAMPLES

Preparation Example 1

Representative preparation examples used in the present invention will be shown below.

1. Eye Drops

Eye drops according to the following formulation was prepared using the general-use method.

After glycerin (2.5 g) and polysorbate 80 (500 mg) were added to sterile purified water, the compound (1 mg) of Example 16 (1) was added to dissolve, sterile purified water was added to a total amount of 100 mL, and this was sterile-filtered with a membrane filter, and filled into a predetermined container to obtain eye drops of the following formulation.

According to the same manner as that described above, eye drops etc. containing 0.1 mg and 0.5 mg of the compound of Example 16 (1) in 100 mL can be prepared. Alternatively, other present invention compounds can be used in place of the compound of Example 16 (1).

2. Ocular Ointment

An ocular ointment of the following formulation was prepared using the general-use method.

A liquid paraffin and white vaseline were heat-sterilized in advance. After the compound (1 mg) of Example 16 (1) was sufficiently kneaded with a liquid paraffin (10 g), white vaseline was added to a total amount of 100 g, and the materials were sufficiently kneaded to obtain an ocular ointment.

INDUSTRIAL APPLICABILITY

Since the present invention compound has strong intraocular pressure lowering action and, further, has no side effects of eyes such as ocular stimulating property (hyperemia, corneal clouding etc.), aqueous humor protein rise etc., it is useful as an excellent agent for preventing and/or treating glaucoma etc.

The invention claimed is:
1. A compound represented by the formula (I):

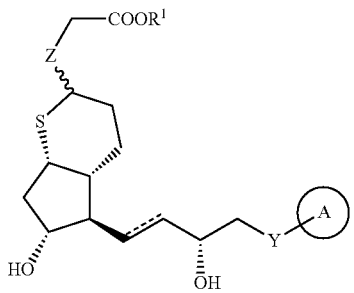

wherein Z represents (1) —(CH$_2$)$_m$—, (2) —CH$_2$—O— or (3) —CH$_2$—S—;
Y represents (1) —O—, (2) —S— or (3) —CH$_2$—;
R$^1$ represents (1) a hydrogen atom or (2) a C1-6 alkyl group;
a ring A represents a benzene ring optionally substituted with 1 to 5 substituents selected from the group consisting of (1) a halogen atom, (2) CF$_3$, (3) OCF$_3$, (4) a C1-4 alkoxy group, (5) a C1-4 alkyl group, (6) a hydroxyl group and (7) a nitrile group;
m represents an integer of 1 or 2,

- - - - - represents a single bond or a double bond,

``````` represents α configuration,

◢ represents β configuration, and

∿∿ represents α configuration, β configuration or an arbitrary mixture thereof, or a salt thereof.

2. The compound according to claim 1, wherein Z is —(CH$_2$)$_m$— wherein all symbols represent the same meanings as those described in claim 1.

3. The compound according to claim 1, wherein Y is —O—.

4. The compound according to claim 1, wherein the compound represented by the formula (I) is a compound selected from the group consisting of
(1) methyl 4-{(2S,4aR,5R, 6R, 7aS)-6-hydroxy-5-[(1E, 3R)-3-hydroxy-4-phenoxy-1-buten-1-yl]octahydrocyclopenta[b]thiopyran-2-yl}butanoate,
(2) methyl 4-{(2R,4aR,5R, 6R, 7aS)-6-hydroxy-5-[(1E, 3R)-3-hydroxy-4-phenoxy-1-buten-1-yl]octahydrocyclopenta[b]thiopyran-2-yl}butanoate,
(3) 4-{(2S,4aR,5R, 6R, 7aS)-6-hydroxy-5-[(1E,3R)-3-hydroxy-4-phenoxy-1-buten-1-yl]octahydrocyclopenta[b]thiopyran-2-yl}butanoic acid,
(4) 4-{(2S,4aR,5R, 6R, 7aS)-6-hydroxy-5-[(1E,3S)-3-hydroxy-5-phenyl-1-penten-1-yl]octahydrocyclopenta[b]thiopyran-2-yl}butanoic acid,
(5) 4-{(2R,4aR,5R, 6R, 7aS)-6-hydroxy-5-[(1E,3R)-3-hydroxy-4-phenoxy-1-buten-1-yl]octahydrocyclopenta[b]thiopyran-2-yl}butanoic acid,
(6) 4-{(2S,4aR,5R, 6R, 7aS)-5-[(1E,3R)-4-(4-fluorophenoxy)-3-hydroxy-1-buten-1-yl]-6-hydroxyoctahydrocyclopenta[b]thiopyran-2-yl}butanoic acid,
(7) 4-{(2S,4aR,5R, 6R, 7aS)-5-[(1E,3R)-4-(3-chlorophenoxy)-3-hydroxy-1-buten-1-yl]-6-hydroxyoctahydrocyclopenta[b]thiopyran-2-yl}butanoic acid,
(8) 4-{(2S,4aR,5R, 6R, 7aS)-6-hydroxy-5-[(1E,3R)-3-hydroxy-4-(3-methylphenoxy)-1-buten-1-yl]octahydrocyclopenta[b]thiopyran-2-yl}butanoic acid,
(9) 4-{(2S,4aR,5R, 6R, 7aS)-5-[(1E,3R)-4-(2-fluorophenoxy)-3-hydroxy-1-buten-1-yl]-6-hydroxyoctahydrocyclopenta[b]thiopyran-2-yl}butanoic acid,
(10) 4-{(2S,4aR,5R, 6R, 7aS)-5-[(1E,3R)-4-(3-fluorophenoxy)-3-hydroxy-1-buten-1-yl]-6-hydroxyoctahydrocyclopenta[b]thiopyran-2-yl}butanoic acid,
(11) 4-[(2S,4aR,5R, 6R, 7aS)-6-hydroxy-5-{(1E,3R)-3-hydroxy-4-(3-(trifluoromethyl)phenoxy]-1-buten-1-yl}octahydrocyclopenta[b]thiopyran-2-yl]butanoic acid,
(12) 4-{(2S,4aR,5R, 6R, 7aS)-6-hydroxy-5-[(1E,3R)-3-hydroxy-4-(2-methoxyphenoxy)-1-buten-1-yl]octahydrocyclopenta[b]thiopyran-2-yl}butanoic acid,
(13) 4-{(2S,4aR,5R, 6R, 7aS)-6-hydroxy-5-[(1E,3R)-3-hydroxy-4-(3-methoxyphenoxy)-1-buten-1-yl]octahydrocyclopenta[b]thiopyran-2-yl}butanoic acid,
(14) 4-{(2S,4aR,5R, 6R, 7aS)-6-hydroxy-5-[(1E,3R)-3-hydroxy-4-(4-methoxyphenoxy)-1-buten-1-yl]octahydrocyclopenta[b]thiopyran-2-yl}butanoic acid,
(15) 4-{(2S,4aR,5R, 6R, 7aS)-6-hydroxy-5-[(1E,3R)-3-hydroxy-4-(2-methylphenoxy)-1-buten-1-yl]octahydrocyclopenta[b]thiopyran-2-yl}butanoic acid,
(16) 4-{(2S,4aR,5R, 6R, 7aS)-6-hydroxy-5-[(1E,3R)-3-hydroxy-4-(4-methylphenoxy)-1-buten-1-yl]octahydrocyclopenta[b]thiopyran-2-yl}butanoic acid,
(17) 4-{(2S,4aR,5R, 6R, 7aS)-5-[(1E,3R)-4-(4-chlorophenoxy)-3-hydroxy-1-buten-1-yl]-6-hydroxyoctahydrocyclopenta[b]thiopyran-2-yl}butanoic acid,
(18) 4-{(2S,4aR,5R, 6R, 7aS)-5-[(1E,3R)-4-(2-chlorophenoxy)-3-hydroxy-1-buten-1-yl]-6-hydroxyoctahydrocyclopenta[b]thiopyran-2-yl}butanoic acid,
(19) 4-[(2S,4aR,5R,6R,7aS)-6-hydroxy-5-{(1E,3R)-3-hydroxy-4-[2-(trifluoromethyl)phenoxy]-1-buten-1-yl}octahydrocyclopenta[b]thiopyran-2-yl]butanoic acid,
(20) 4-[(2S,4aR,5R, 6R, 7aS)-6-hydroxy-5-{(1E,3R)-3-hydroxy-4-[4-(trifluoromethyl)phenoxy]-1-buten-1-yl}octahydrocyclopenta[b]thiopyran-2-yl]butanoic acid,

(21) 4-{(2S,4aR,5R, 6R, 7aS)-6-hydroxy-5-[(3R)-3-hydroxy-4-phenoxybutyl]octahydrocyclopenta[b]thiopyran-2-yl}butanoic acid,
(22) 2-propanyl 4-{(2S,4aR,5R, 6R, 7aS)-6-hydroxy-5-[(3R)-3-hydroxy-4-phenoxybutyl]octahydrocyclopenta[b]thiopyran-2-yl}butanoate,
(23) 2-propanyl 4-{(2S,4aR,5R, 6R, 7aS)-6-hydroxy-5-[(1E,3R)-3-hydroxy-4-phenoxy-1-buten-1-yl]octahydrocyclopenta[b]thiopyran-2-yl}butanoate,
(24) 2-propanyl 4-{(2S,4aR,5R, 6R, 7aS)-5-[(1E,3R)-4-(3-chlorophenoxy)-3-hydroxy-1-buten-1-yl]-6-hydroxyoctahydrocyclopenta[b]thiopyran-2-yl}butanoate,
(25) 2-propanyl 4-{(2S,4aR,5R, 6R, 7aS)-6-hydroxy-5-[(1E,3R)-3-hydroxy-4-(3-methylphenoxy)-1-buten-1-yl]octahydrocyclopenta[b]thiopyran-2-yl}butanoate,
(26) 2-propanyl 4-{(2S,4aR,5R, 6R, 7aS)-5-[(1E,3R)-4-(3-fluorophenoxy)-3-hydroxy-1-buten-1-yl]-6-hydroxyoctahydrocyclopenta[b]thiopyran-2-yl}butanoate,
(27) 2-propanyl 4-{(2S,4aR,5R, 6R, 7aS)-5-[(1E,3R)-4-(4-fluorophenoxy)-3-hydroxy-1-buten-1-yl]-6-hydroxyoctahydrocyclopenta[b]thiopyran-2-yl}butanoate,
(28) 2-propanyl 4-{(2S,4aR,5R, 6R, 7aS)-6-hydroxy-5-[(1E,3R)-3-hydroxy-4-(3-methoxyphenoxy)-1-buten-1-yl]octahydrocyclopenta[b]thiopyran-2-yl}butanoate,
(29) 2-propanyl 4-{(2S,4aR,5R, 6R, 7aS)-6-hydroxy-5-[(1E,3R)-3-hydroxy-4-(2-methoxyphenoxy)-1-buten-1-yl]octahydrocyclopenta[b]thiopyran-2-yl}butanoate and
(30) 2-propanyl 4-[(2S,4aR,5R, 6R, 7aS)-6-hydroxy-5-{(1E,3R)-3-hydroxy-4-[3-(trifluoromethyl)phenoxy]-1-buten-1-yl}octahydrocyclopenta[b]thiopyran-2-yl]butanoate.

5. A pharmaceutical composition comprising the compound represented by the formula (I) according to claim 1, or a salt thereof.

6. The pharmaceutical composition according to claim 5, wherein the compound represented by the formula (I) according to claim 1, or a salt thereof.

7. A method of treating an ocular disease, comprising a compound represented by the formula (II):

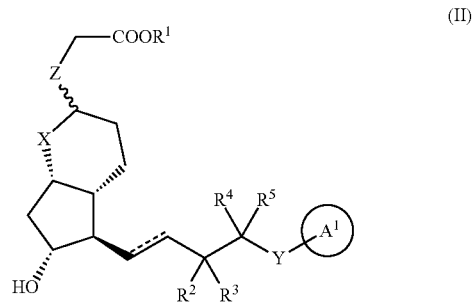

wherein Z represents (1) —(CH$_2$)$_m$—, (2) —(CH$_2$)—O— or (3) —CH$_2$—S—;
Y represents (1) —O—, (2) —S— or (3) —CH$_2$—;
R$^1$ represents (1) a hydrogen atom or (2) a C1-6 alkyl group;
X represents (1) —O— or (2) —S—;
a ring A$^1$ represents a C3-10 carbocyclic ring optionally substituted with 1 to 5 substituents selected from the group consisting of (1) a halogen atom, (2) CF$_3$, (3) OCF$_3$, (4) a C1-4 alkoxy group, (5) a C1-4 alkyl group, (6) a hydroxyl group and (7) a nitrile group, or a 3- to 10-membered heterocyclic ring optionally substituted with 1 to 5 substituents selected from the group consisting of (1) a halogen atom, (2) CF$_3$, (3) OCF$_3$, (4) a C1-4 alkoxy group, (5) a C1-4 alkyl group, (6) a hydroxyl group and (7) a nitrile group;
R$^2$, R$^3$, R$^4$ and R$^5$ each independently represent (1) a hydrogen atom, (2) a C1-4 alkyl group, (3) a halogen atom or (4) a hydroxyl group, or a salt thereof, a solvate thereof, or a prodrug thereof.

8. A method of treating an ocular disease, comprising administering an effective amount of the compound represented by the formula (I) according to claim 1, or a salt thereof to a mammal.

9. The method according to claim 8, wherein the ocular disease is glaucoma, ocular hypertension, macular edema, macular degeneration, retina and optic nerve tensile force rise, myopia, hypermetropia, astigmatism, dry eye, retinal detachment, cataract, intraocular pressure rise due to trauma or inflammation, intraocular pressure rise due to a drug, or intraocular pressure rise after operation.

* * * * *